United States Patent
Gan

(10) Patent No.: US 10,543,017 B2
(45) Date of Patent: Jan. 28, 2020

(54) SURGICAL DEVICE

(71) Applicant: LIVAC IP CO PTY LTD, Toorak, Victoria (AU)

(72) Inventor: Philip Gan, Warrnambool (AU)

(73) Assignee: Livac IP Co. Pty. Ltd., Toorak, Victoria (AU)

( * ) Notice: Subject to any disclaimer, the term of this patent is extended or adjusted under 35 U.S.C. 154(b) by 151 days.

(21) Appl. No.: 15/741,208

(22) PCT Filed: Jun. 29, 2016

(86) PCT No.: PCT/AU2016/000228
§ 371 (c)(1),
(2) Date: Dec. 29, 2017

(87) PCT Pub. No.: WO2017/000016
PCT Pub. Date: Jan. 5, 2017

(65) Prior Publication Data
US 2018/0177525 A1    Jun. 28, 2018

(30) Foreign Application Priority Data

Jun. 30, 2015 (AU) ............................. 2015902555
Apr. 21, 2016 (AU) ............................. 2016901497

(51) Int. Cl.
*A61B 17/34* (2006.01)
*A61B 17/02* (2006.01)
*A61M 1/00* (2006.01)

(52) U.S. Cl.
CPC ...... *A61B 17/3423* (2013.01); *A61B 17/0218* (2013.01); *A61M 1/0058* (2013.01); *A61B 2217/005* (2013.01); *A61B 2217/007* (2013.01)

(58) Field of Classification Search
CPC ..................... A61B 17/3423; A61B 17/0218
See application file for complete search history.

(56) References Cited

U.S. PATENT DOCUMENTS 5,913,852 A    6/1999  Magram
2005/0234304 A1 * 10/2005 Dewey ............... A61B 17/0206
                                                   600/210

(Continued)

OTHER PUBLICATIONS

International Preliminary Report on Patentability for International Application No. PCT/AU2016/000228, dated Jul. 21, 2017. (17 pages).

(Continued)

*Primary Examiner* — Christian A Sevilla
(74) *Attorney, Agent, or Firm* — Dickinson Wright, PLLC; Michael E. Noe, Jr.

(57) ABSTRACT

The present invention provides a surgical device comprising: an elongate body with a proximal end and a distal end, the elongate body comprising an abutment portion comprising a pair of integral outwardly flaring elongate wings which between them define a channel adapted for receiving a longitudinally adjacent trocar; and attachment means capable of attaching the elongate body to tubing. Also provided are methods of manufacturing the device of the invention, methods for inserting the device of the invention into an incision in a patient, and methods for delivering suction or fluid to an internally located apparatus using the device of the invention.

10 Claims, 22 Drawing Sheets

(56) References Cited

U.S. PATENT DOCUMENTS

| | | | |
|---|---|---|---|
| 2011/0196411 A1* | 8/2011 | Forsell | A61B 17/0469 606/191 |
| 2011/0313250 A1* | 12/2011 | Kleyman | A61B 17/3423 600/123 |
| 2012/0089093 A1 | 4/2012 | Trusty | |
| 2013/0218159 A1* | 8/2013 | Kappel | A61B 17/0218 606/45 |

OTHER PUBLICATIONS

International Search Report and Written Opinion for International Application No. PCT/AU2016/000228, dated Sep. 7, 2016. (8 pages).

* cited by examiner

A

B

A

B

A

B

A

B

SURGICAL DEVICE

TECHNICAL FIELD

The present invention relates to a surgical device, a method of using a surgical device and a method of manufacturing a surgical device. More particularly, this invention relates to a surgical device for use in providing suction or fluid, such as gas or liquid, to an internally located apparatus, such as a sucker-irrigator or a retractor, during surgery.

BACKGROUND

Laparoscopic surgery is carried out by passing trocars through multiple small incisions, or by using Single Port Laparoscopic Surgery (SPLS) which utilizes only a single incision and single port. The benefits of laparoscopic surgery and/or SPLS have been reported to include reduced postoperative pain, tissue trauma and scarring as well as faster recovery from surgical procedures.

The accumulation of blood and other fluid during surgery interferes with many procedures, such as cholecystectomies. Accordingly, suction is used during laparoscopic surgery for the evacuation of blood, bile, pus, irrigation fluid and/or vapours and the irrigation of tissue using saline solutions and the like is used to assist in this process. Sucker-irrigator apparatus are usually handheld devices using one actuator for suction and another actuator for irrigation (typically controlled by a trumpet valve mechanism), and which comprise a long rigid tube for insertion into the patient's abdomen through the laparoscopic port. Typically two flexible hoses extend from the handpiece controller: one hose is connected to a suction canister, which in turn is connected to wall suction, and the other hose is attached to a source of pressurised irrigation fluid. The handpiece controller determines whether irrigation or suction is applied through the long rigid tube entering the abdomen. The rigid tube of sucker-irrigators is commonly designed to fit in a 5 mm laparoscopic trocar, although wider sucker-irrigator tubes having a diameter of 10 mm are used with larger laparoscopic trocars when evacuating thicker material such as clots and particulate matter, and 3 mm sucker-irrigators are available, but less frequently used. When a sucker-irrigator is required, a surgeon will typically withdraw at least one of the laparoscopic instruments being used from its laparoscopic trocar and insert the sucker-irrigator into the laparoscopic trocar. This procedure may take some time, during which period bleeding may continue, further obscuring the surgeon's view. On occasion, an additional trocar may be inserted to house a sucker-irrigator so that suction-irrigation may be carried out at the same time as haemostasis. Conventional sucker-irrigators typically use screw-in or click in rigid tubing to attach to the handpiece controller.

Furthermore, in accessing target tissue to be operated upon, medical personnel typically use a retractor system or apparatus to hold adjacent tissue to be retracted from the operating field. This is particularly the case where the laparoscopic procedure is carried out in the abdomen of a patient and obstructive tissue needs to be temporarily and gently moved out of the way. Conventional retractor systems apply a positive force to the under-surface of the organ to be retracted. Alternatively, vacuum retraction apparatus are available which are internally located within the patient and which are connected to suction apparatus via a length of tubing passing through an incision in the abdominal wall, as shown in FIG. 1A. However, such tubing is prone to compression, angulation or bending as it passes through the incision, by the tissues themselves or the adjacent laparoscopic trocar. This interrupts the suction provided and thus the efficiency of tissue retraction. This particularly happens where skin incisions are too small and the trocar and tubing are tightly fitted within the incision. Suction interruptions during surgical procedures are inconvenient and time-consuming, and can interfere with the surgical procedure. Where the tubing passes through a channel within a single port laparoscopic surgery device such as the SILS™ Port, it will be subject to even higher compressive forces as the adjacent laparoscopic instruments are angulated. As such, the tubing requires protection from compression by drawing it through a laparoscopic trocar within the SILS™ Port (FIG. 1B). Such an arrangement, however, is bulky and requires additional steps which increase the time required.

Laparoscopic procedures also involve insufflation wherein inert, non-toxic gases, such as carbon dioxide, are insufflated into a body cavity to provide internal room (pneumoperitoneum) for surgical manipulation and viewing by elevating the abdominal wall. The incisions used in laparoscopic surgery, while small, may permit leakage of the insufflation gas from the body cavity (under positive pressure) from around the trocars inserted, particularly where the tubing of vacuum retractor systems or apparatus is passed adjacent to the trocar. This insufflation gas leakage may reduce the dimensions of the pneumoperitoneum, making it necessary to insufflate further gas into the body cavity which wastes the gas ($CO_2$) and may interfere with the surgical procedure. It is a technical challenge to cut an incision in a patient's abdominal wall that is large enough to accommodate the laparoscopic trocar and retractor system tubing without constricting the tubing, yet is small enough to minimise gaps and reduce leakage of insufflation gas.

It is desirable to provide a device and/or method that will alleviate one or more of the shortcomings of suction and/or irrigator systems and apparatus and their use.

SUMMARY OF INVENTION

The present invention is broadly directed to a novel and inventive surgical device and method which has particular application in laparoscopic surgery. Conventional methods involving the use of vacuum retractors in laparoscopic surgery rely on simply connecting the flexible tubing of the vacuum retractor device to a suction hose leading to the suction source whilst allowing the tubing to pass alongside a laparoscopic trocar or through an incision in a patient's abdomen. Such tubing is at risk of collapse at points of bending or other external compression forces. Any collapse in the tubing interrupts the suction provided to the vacuum retractor and can disrupt the retraction. The present invention has arisen after the present inventor developed a method and device for connecting the tubing of a vacuum retractor device to a suction hose which is more resistant to collapse, reducing interruption in the vacuum forces provided to the surgical apparatus. Suction-irrigation devices have a rigid tube which is always inserted through a laparoscopic port, and its use thereby results in the displacement of other instruments from that laparoscopic trocar. The present invention has also arisen after the present inventor developed a method and device for delivering suction forces and irrigation fluids to a suction-irrigation apparatus which does not necessitate the displacement of other instruments from the laparoscopic trocar. Furthermore, the device of the present invention substantially reduces leakage of $CO_2$ between the device and laparoscopic trocars.

In one aspect, there is provided a surgical device comprising:
    an elongate body with a proximal end and a distal end, the elongate body comprising an abutment portion comprising a pair of integral outwardly flaring elongate wings which between them define a channel adapted for receiving a longitudinally adjacent trocar; and
    attachment means capable of attaching the elongate body to tubing.

The elongate body may be circular, elliptical, triangular, crescent-shaped or kidney-shaped in cross-section.

It will be appreciated that the trochar used in the present invention is a laparoscopic trocar, but that other functionally equivalent cylindrical bodies may also be used.

In the first embodiment, the abutment portion comprises a laterally extending flange or collar in the form of a pair of integral outwardly flaring elongate wings which between them define a channel. The channel may be shaped to receive a longitudinally adjacent laparoscopic trocar. Preferably, the abutment portion comprises at least one pair of outwardly flaring elongate wings which are integral with the elongate body, and extend laterally therefrom, defining a channel. The dimensions of the wings may be longer at the proximal end than at the distal end of the elongate body, defining a relatively deeper channel at the proximal end than at the distal end. Alternatively, the abutment portion may comprise at least two pairs of outwardly flaring elongate wings which are integral with the elongate body, wherein the at least two pairs of wings are different in dimension and are spaced or located along the tubing or elongate body of the device. One pair of wings may be relatively smaller in dimension, while the other pair of wings may be relatively larger in dimension and separated from the smaller pair of wings by a length of tubing. It will be appreciated that in use, the smaller pair of wings may be braced against a 5 mm trocar, while the larger pair of wings may be braced against a 12 mm trocar. In the latter instance, the smaller pair of wings will have been inserted into the patient, before the larger pair of wings is braced against the 12 mm trocar.

The wings define a channel or otherwise elongate curved surface which corresponds or substantially corresponds to the side of the longitudinally adjacent laparoscopic trocar, when the device is abutted or braced against it. It will be appreciated that the device may be smaller in cross-section than the trocar, and when the device is braced against the trocar within an incision in a patient, the wings fit against and around the side of the trocar, thereby minimising the opposing gaps formed on either side of the device and between the device and the margins of the incision, and substantially occluding and/or substantially sealing the gaps formed between the device and the trocar, when the device and the trocar are placed longitudinally adjacent to one another. The wings may be between 5 mm and 160 mm in length. Preferably, the wings are about 20 mm in length. It will be appreciated that, in embodiments where the dimensions of the wings are longer at the proximal end than at the distal end of the elongate body, the relatively deeper channel defined at the proximal end of the elongate body is adapted to receive a longitudinally adjacent trocar of larger diameter (such as a trocar with a diameter of up to about 15 mm) than the relatively shallower channel defined by the wings at the distal end. The relatively shallower channel defined by the wings at the distal end of the elongate body is adapted to receive a longitudinally adjacent trocar of smaller diameter (such as a trocar with a diameter of about 5 mm).

In embodiments in which the abutment portion comprises more than one pair of wings of different dimensions, the pairs of wings may be separated from each other by a variable length of tubing, such that when a larger trocar is used, the smaller dimensioned pair of wings is pushed by a user into the abdominal cavity and the relatively larger dimensioned pair of wings is then braced against a correspondingly larger trocar within the abdominal wall. When a smaller trocar is used, the smaller dimensioned wings will be braced against that trocar whilst the larger dimensioned wings will remain external to the patient.

In the first embodiment, the wings may be rigid. Alternatively, the wings may be flexible, conformable and/or deformable. The abutment portion may be inflatable, fluid-filled or gel-filled. The inflatable abutment portion may be inflated when the device is in place within the incision, adjacent to the trocar, such that the inflated abutment portion braces against the trocar, substantially filling the gaps formed between the trocar and the device, and between these and the margins of the incision. The abutment portion may comprise a pair of fluid-filled or gel-filled wings that are easily deformable or malleable and capable of conforming to the shape of the side of the trocar.

In the first embodiment, the elongate body and the abutment portion may be integral, wherein the abutment portion comprises a pair of outwardly flaring elongate wings defining a channel extending the length of the elongate body.

In the first embodiment, the attachment means may comprise at least one clasp capable of engaging tubing. The clasp may comprise an annular projection extending from the elongate body through which the tubing may be threaded. Alternatively, the clasp may comprise a collar or clip for lateral engagement with the tubing. Preferably the attachment means comprises at least two clasps, one disposed at the proximal end of the elongate body of the device and the other disposed at the distal end of the elongate body. Typically, the clasp(s) extend laterally from an opposed side of the elongate body to that of the pair of outwardly flaring wings.

The tubing to which the first embodiment is attached may be silicone tubing. Typically, the silicone tubing has a diameter of between about 4 mm to 7 mm. The external suction hose leading to the source of suction is typically in the order of 10 mm diameter.

Alternatively, the attachment means may comprise glue applied between the wing assembly and the tubing; the tubing effectively replacing the elongate body.

In a second embodiment, the elongate body comprises:
    an elongate hollow internal leg comprising a distal end portion and an internal leg axis;
    an elongate hollow external leg comprising a proximal end portion and an external leg axis; and
    an optional bend intermediate the proximal end portion and the distal end portion wherein the internal leg and the external leg axes intersect.

The bend may be configured to reduce interference between the external suction hose and the laparoscopic trocar against which the body is apposed. The bend may comprise a length of flexible tubing, leading to the external leg portion.

Like the first embodiment, the abutment portion of the second embodiment may comprise a laterally extending flange or collar defining a channel, which is shaped to receive a longitudinally adjacent trocar. The flange or collar may be in the form of a pair of integral outwardly flaring elongate wings which between them define the channel. Preferably, the pair of outwardly flaring elongate wings are integral with the elongate body, and extend laterally therefrom, defining a channel. The dimensions of the wings may be longer at the proximal end of the elongate body than at the distal end of the elongate body, defining a relatively deeper channel at the proximal end than at the distal end.

The wings define a channel or otherwise elongate curved surface which corresponds or substantially corresponds to the side of the longitudinally adjacent trocar, when the device is abutted or braced against it. It will be appreciated that the device may be smaller in cross-section than the trocar, and when the device is braced against the trocar within an incision in a patient, the wings fit against and around the side of the trocar, thereby minimising the opposing gaps formed on either side of the device and between the device and the margins of the incision, and substantially occluding and/or substantially sealing the gaps formed between the device and the trocar, when the device and trocar are placed longitudinally adjacent to one another. The wings may be between 5 mm and 160 mm in length. Preferably, the wings are about 20 mm in length.

The wings may be rigid. Alternatively, the wings may be flexible, conformable and/or deformable. The abutment portion may be inflatable, fluid-filled or gel-filled. The inflatable abutment portion may be inflated when the device is in place within the incision, adjacent to the trocar, such that the inflated abutment portion braces against the trocar, substantially filling the gaps formed between the trocar and the device, and between these and the margins of the incision. The abutment portion may comprise a pair of fluid-filled or gel-filled wings that are easily deformable or malleable and capable of conforming to the shape of the side of the trocar.

In the second embodiment, the abutment portion may be detachable from the internal leg. The abutment portion may be attachable to the internal leg so that it may be located at a desired position along the length of the internal leg. The abutment portion may be slidably attachable to the internal leg so that it may be moved along the internal leg and fixed into position at a desired location. The abutment portion may be detachable from the internal leg and attachable to the internal leg.

In the second embodiment, the abutment portion may be intermediate the bend and the distal end portion.

In the second embodiment, the attachment means capable of connecting the elongate body to tubing may comprise:
  the distal end portion of the elongate hollow internal leg wherein the distal end portion is adapted to connect to internal tubing; and
  the proximal end portion of the elongate hollow external leg wherein the proximal end portion is adapted to connect to external tubing.

The distal end portion of the internal leg may include hooks for engaging internal tubing. The hooks may be barb-shaped, and may be radially disposed around the outer wall of the internal leg, and spaced from the end thereof. The hooks may comprise two (2), three (3), four (4) or more hooks.

The distal end portion may also include an annular shoulder or buttress located intermediate the hooks and the abutment portion. The annular shoulder may be in the form of an integral outwardly facing continuous collar spaced from the hooks. The annular collar may be shaped and dimensioned to correspond to the end of the internal tubing such that it braces against the end of the internal tubing when the distal end portion is placed therein and the adjacent collar and tubing together provide a smooth continuous external surface so as to prevent catching on tissues or port channels as the device is inserted and withdrawn. The external diameter of the annular shoulder may be between 5 mm and 10 mm, preferably about 7.5 mm.

It will be appreciated that the external diameter of the annular shoulder may be such that the internal tubing can stretch over the distal end portion.

The proximal end portion may comprise a widened portion for engaging or bracing against the external tubing. The widened portion may be spaced from the end of the external leg, and may be shaped and dimensioned to correspond to the end of the external tubing such that it substantially seals against the external tubing when the proximal end portion is placed therein.

The proximal end portion of the external leg may include hooks for engaging the external tubing. The hooks may be barb-shaped, and may be radially disposed around the outer wall of the external leg, and spaced from the end thereof. The hooks may comprise two (2), three (3), four (4) or more hooks.

It will be appreciated that the second embodiment of the device of the invention may function as a connector when connected to internal and external tubing, forming a conduit therebetween.

The second embodiment of the device may further comprise a plug portion located on the internal leg. The plug portion may be in the form of an integral bulbous portion which, when the device is placed within the lumen of co-axially extending tubular housing such as a laparoscopic single incision port or other collar device, braces against the internal walls of the housing, and substantially fills it. The plug portion may be between 5 mm and 8 mm in external diameter, preferably about 6 mm.

The bend may be angular or gently curved. The angle of intersection of the internal leg and the external leg axes may be between 90 degrees and 160 degrees. Preferably the angle of intersection is 120 degrees.

The internal leg of the device may have an internal diameter of between 2.5 mm and 6 mm, preferably about 3 mm. Preferably, the internal diameter of the device is substantially equivalent to, and at least not significantly less than, the internal diameter of the internal tubing so as not to increase resistance to fluid flow. The internal leg of the device may have an external diameter of between 4 mm and 8 mm, preferably between 5 mm and 6 mm. The length of the internal leg may be between 50 mm and 160 mm, preferably between 74 mm and 110 mm, from the end of the internal leg to the bend (embodiments with longer lengths for obese patients), and between 15 mm and 145 mm in length from the end of the internal leg to the abutment portion, preferably about 59 mm (depending upon the chosen length of abutment portion). Embodiments with longer lengths may be produced such as, for example, to suit obese patients. The external leg may be between 20 mm and 75 mm, preferably about 56 mm. The widened portion on the external leg may be spaced between 10 mm and 30 mm from the end of the external leg, preferably about 23 mm. The widened portion may be between 8 mm and 12 mm in external diameter, preferably about 10.5 mm. The external diameter of the end of the external leg may be between 4 mm and 8 mm, preferably about 5.3 mm. The overall length of the device may be between 60 mm and 185 mm, preferably about 131 mm.

The tubing may be silicone tubing, such as that conventionally used in surgical procedures.

Other devices may be attached to the end of the tubing of the first embodiment or the internal tubing of the second embodiment, such as a rigid suction-irrigation nozzle tip. Such an internal nozzle tip would typically be glued or otherwise attached to the tubing. The internal nozzle tip may comprise multiple holes along a side, and an open hole at its tip. The internal nozzle tip may optionally comprise at least one recess or gripping surfaces for gripping with, for instance, a pair of forceps. Other devices may be attached to the internal tubing of the second embodiment, such as retractors.

In another aspect of the invention, there is provided a kit comprising the device of the invention.

The kit may further comprise tubing and/or a surgical apparatus including a retractor, a sucker and/or an irrigator.

In another aspect of the invention, there is provided a method for manufacturing the first embodiment of the device of the invention.

The method for manufacturing the first embodiment of the device of the invention may comprise
  manufacturing an elongate body with a proximal end and a distal end, the elongate body comprising an abutment portion comprising a pair of integral outwardly flaring elongate wings which between them define a channel adapted for receiving a longitudinally adjacent trocar; and
  manufacturing attachment means capable of attaching the elongate body to tubing.

The method for manufacturing the first embodiment of the device of the invention may be carried out by using techniques known in the field of silicone injection moulding.

The device of the first embodiment may be manufactured from a bio-compatible, sterilisable plastic material such as polycarbonate (Lexan®, Makrolon®) or other suitable material. These embodiments may be disposable.

In another aspect of the invention, there is provided a method for inserting the first embodiment of the invention into an incision in a patient, the method comprising the steps of:
  inserting a laparoscopic trocar into the incision;
  withdrawing the trocar from the incision;
  inserting the tubing into the incision, the tubing optionally connected to a sucker-irrigator apparatus;
  inserting the first embodiment of the device of the invention into the incision, optionally attached to the tubing; and
  inserting the trocar into the incision adjacent to the device until the side of the trocar is received by the abutment portion.

In embodiments wherein the abutment portion comprises more than one pair of wings of different dimensions, the steps of inserting the first embodiment of the device of the invention into the incision and inserting the trocar into the incision adjacent to the device until the side of the trocar is received by the abutment portion may comprise inserting the smaller pair of wings into the incision until the larger pair of wings braces against the trocar.

In another aspect of the invention, there is provided a method for manufacturing the second embodiment of the device of the invention, the method comprising the steps of:
  producing the internal leg with the distal end portion and a first complementary end;
  producing the external leg with the proximal end portion and a second complementary end; and
  attaching the first complementary end to the second complementary end.

The first complementary end may be a female end and the second complementary end may be a male end, and visa versa.

The male end and the female end may be correspondingly tapered to facilitate insertion of the male end into the female end. The taper may be between 1.5 degrees and 5 degrees, preferably about 2 degrees.

The method for manufacturing the second embodiment of the invention may further comprise the step of applying adhesive to the inside of the female end and/or to the outside of the male end.

The method for manufacturing the second embodiment of the invention may further comprise the steps of:
  producing the abutment portion; and
  attaching the abutment portion to the internal leg.

The device of the second embodiment may be manufactured from a bio-compatible, sterilisable plastic material such as polycarbonate (Lexan®, Makrolon®) or other suitable material. These embodiments may be disposable. Alternatively, the device may be machined from surgical grade steel. Such embodiments may be sterilised and re-used.

The abutment portion may be manufactured from the same material as the device in embodiments wherein the abutment portion is rigid. In other embodiments, where the abutment portion is flexible, it may be manufactured from the wide variety of bio-compatible, sterilisable materials such as those known to a person skilled in the art.

The device of the second embodiment may be preferably manufactured using injection-moulding methods into a cavity injection-mould.

The method for manufacturing the device of the second embodiment of the invention may include three dimensional (3D) printing or additive manufacturing using photocuring resins or thermoplastic materials such as polylactic acid (PLA), acrylonitrile butadiene styrene (ABS), nylon, polycarbonate (PC), polyphenylsulfone (PPSU), or high-density polyethylene (HDPE).

In another aspect of the invention, there is provided a method for inserting the second embodiment of the invention into a patient, the method comprising the steps of:
  inserting the distal end portion of the internal leg into the internal tubing;
  inserting the internal leg with internal tubing into an incision in a patient; and
  inserting a trocar into the incision adjacent to the device until the side of the trocar is received by the abutment portion.

The step of inserting the internal leg with internal tubing into the incision may include inserting the internal leg until the wings abut the incision.

The step of inserting the internal leg with internal tubing into the incision may include inserting the device into the lumen of co-axially extending tubular housing, such as a SILS™ Port or other collar device such as the LiVac™ Bevel. The lumen may include a channel of the SILS™ Port or a secondary channel of the LiVac™ Bevel.

The method may further include the steps of cutting a section of the internal tubing and connecting it to the end of the external leg of the device. A conventional connector may be used to connect the end of the tubing to suction hose.

It will be appreciated that the device of the second embodiment of the invention may be used as a conventional device outside of the abdomen of a patient, for example, where single port devices, such as the Applied Medical GelPOINT, are used.

In another aspect of the invention, there is provided a method for delivering suction or fluid to an internally located apparatus, the method comprising the steps of:
  inserting the distal end portion of the device of the invention into the internal tubing, wherein the internal tubing is connected to the internally located apparatus;
  inserting the internal leg with internal tubing into an incision in a patient;

inserting a trocar into the incision adjacent to the device until the side of the trocar is received by the abutment portion;

inserting the proximal end portion of the device into the external tubing connected to a suction or fluid source; and activating the suction or fluid source.

The internally located apparatus may be a surgical apparatus such as a sucker-irrigator.

The fluid may be gas, such as $CO_2$, or liquid, such as saline.

The step of inserting the internal leg with internal tubing into an incision may include inserting the internal leg until the bend abuts the incision.

The step of inserting the internal leg with internal tubing into the incision may include inserting the device into the lumen of co-axially extending tubular housing, such as a SILS™ Port or other collar device such as the LiVac™ Bevel. The lumen may include a channel of the SILS™ Port or a secondary channel of the LiVac™ Bevel.

The step of activating the suction or fluid source may comprise releasing or removing an occlusion applied to the external tubing.

The trocar may be a conventional laparoscopic trocar such as, but not restricted to, a 5 mm, 12 mm or 15 mm trocar.

It will be appreciated that the device and methods of the invention may be used for irrigation or for blowing of gas, such as $CO_2$, into the pneumoperitoneum.

The device may be connected to internal tubing which may be kept within the abdomen throughout the surgical operation. The device may be connected to suction or irrigation apparatus which may be hand-held, foot-operated, or machine-controlled, such as by way of voice activation commands.

Any discussion of the prior art throughout the specification should in no way be considered as an admission that such prior art is widely known or forms part of the common general knowledge in the field.

As used herein, except where the context requires otherwise, the term "comprise" and variations of the term, such as "comprising", "comprises" and "comprised", are not intended to exclude further additives, components, integers or steps.

BRIEF DESCRIPTION OF DRAWINGS

In order that the present invention may be readily understood and put into practical effect, reference will now be made to the accompanying illustrations, wherein like reference numerals refer to like features.

DETAILED DESCRIPTION OF INVENTION

Figure 1A:
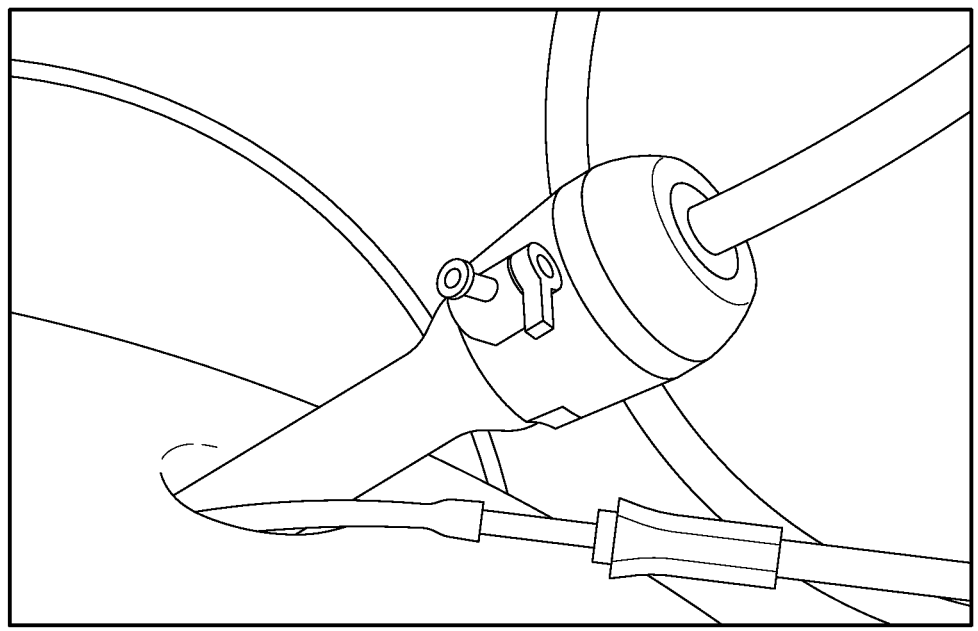
FIG. 1 shows (A) a photograph of a 12 mm Covidien trocar with silicone tubing passing through an incision adjacent to the laparoscopic trocar, to illustrate conventional use of tubing with retractor apparatus and (B) retractor apparatus tubing passing through a SILS™ port, showing how the tubing has been drawn through a 5 mm trocar within the SILS™ port to prevent compression.

The inventor has developed a device for use in medical and surgical procedures for connecting tubing to internally located retractors and sucker-irrigators placed within a patient. The device has particular application in laparoscopic procedures. The first embodiment of the device of the invention may be used for various different surgical applications, including suction, irrigation, and/or blowing of $CO_2$ gas, while the second embodiment of the device of the invention is particularly useful for connecting a retractor to suction apparatus.

As shown in FIGS. 2 to 5, the surgical device (10) comprises an elongate body (11) with a proximal end (11.1) and a distal end (11.2), the elongate body (11) comprising an abutment portion (26) adapted for receiving a longitudinally adjacent trocar (17). The device (10) also comprises attachment means (31) capable of attaching the elongate body (11) to tubing (19.1).

In the first embodiment, shown in FIGS. 2A and 2B, the abutment portion (26) comprises a laterally extending flange or collar, in the form of a pair of integral outwardly flaring elongate wings (28) which between them define a channel (30) shaped to receive the side of a trocar (17).

Figure 16:
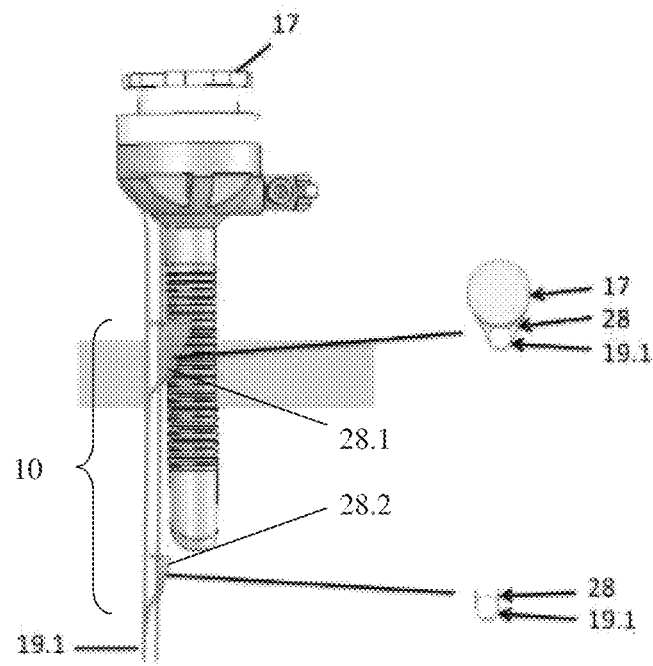
FIG. 16 shows (A) a diagrammatic representation of a first embodiment of the device of the invention with two pairs of wings of different dimensions, in use with a trocar of larger diameter and (B) a diagrammatic representation of an embodiment with one pair of wings defining a channel which is deeper at the proximal end than at the distal end of the elongate body, wherein the cross-section of the tubing and wings together form a crescent.
Figure 16:
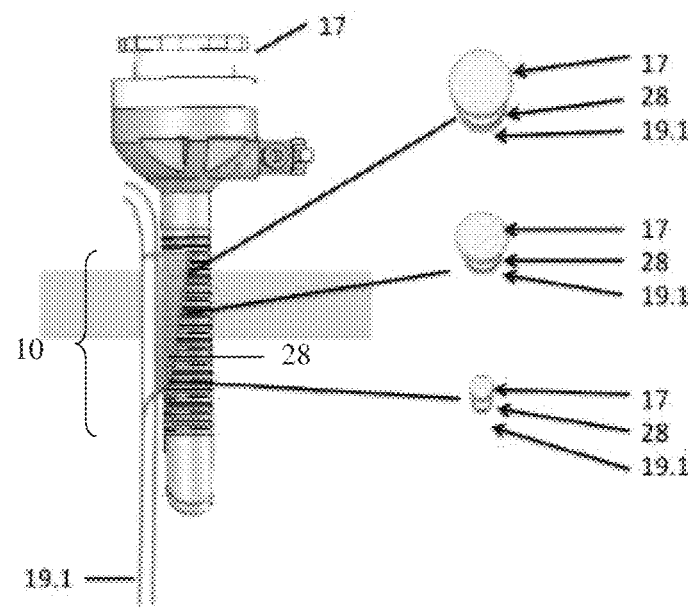
Figure 17:
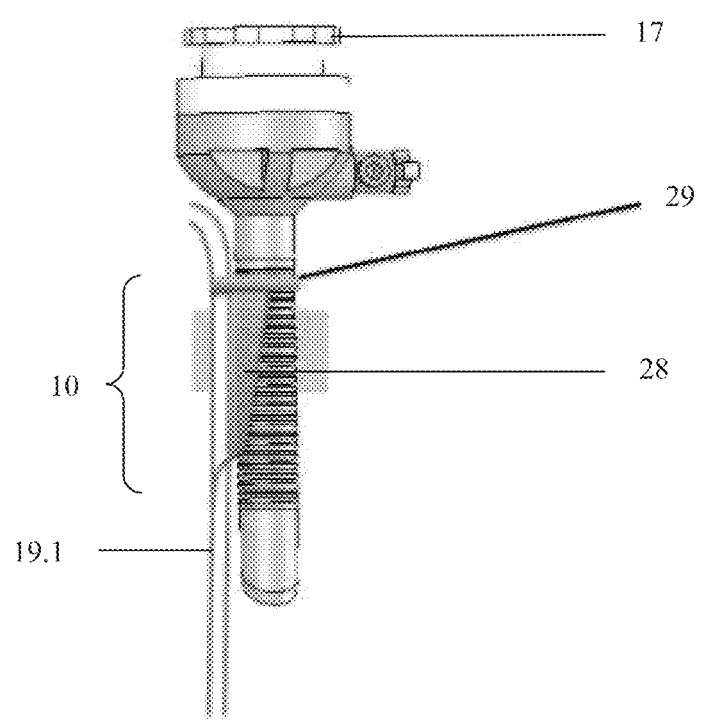
FIG. 17 shows a diagrammatic representation of the embodiment of FIG. 16B with a retainer.

The first embodiment may comprise at least two pairs of wings (28.1, 28.2) which are different in dimension, as shown in FIG. 16A. In this embodiment, the at least two pairs of wings (28.1, 28.2) are spaced along the elongate body (11), with the smaller pair of wings (28.2) disposed towards the distal end (11.2) of the elongate body (11) and the larger pair of wings disposed towards the proximal end (11.1) of the elongate body (11). As shown in FIG. 16A, the elongate body is separated by tubing into two sections which are delineated by the smaller and larger pairs of wings. It will be appreciated that the smaller pair of wings (28.2) engages a trocar (17) of relatively smaller diameter while the larger pair of wings (28.1) engages a trocar (17) of relatively larger diameter. In use, when the larger pair of wings (28.2) is braced against a trocar (17) of larger diameter, the smaller pair of wings (28.2) is located inside the incision in the patient. Similarly, when the smaller pair of wings (28.2) is braced against a trocar (17) of smaller diameter, the larger pair of wings (28.1) is located outside the incision of the patient. The first embodiment may also comprise a retainer (29) in the form of a belt which grips the port (17) and locates the device 910) against the trocar (17) when used (FIG. 17).

Attachment means (FIG. 2A, 31) in the form of a pair of clasps are disposed at the proximal end (11.1) and at the distal end (11.2) of the elongate body (11) of the device (10), and facilitate attachment of the device (10) to the tubing (19.1). Alternatively, the attachment means may be an adhesive applied between the tubing and the conformal channel along the body as shown in FIG. 2B.

The first embodiment of the device (10) may be made from flexible material such as silicone and is attached to the side of tubing for insertion through an incision in the abdomen of the patient during laparoscopic procedures.

The second embodiment of the device provided by the invention may be made from non-compressible material and is inserted through an incision in the abdomen of a patient during laparoscopic procedures. It is intended to extend through the incision, connecting the internal tubing placed within the body cavity of the patient and the external tubing, which leads thereon to the source of suction (or irrigation/gas source in other applications). The second embodiment of the device is non-compressible, and is able to withstand suction pressures of between 0 to −760 mmHg, such as those used for operating retractor suction systems and apparatus during surgical procedures, and to withstand the external forces applied within the abdominal wall and as applied by the laparoscopic ports with which it is used.

Figure 3:
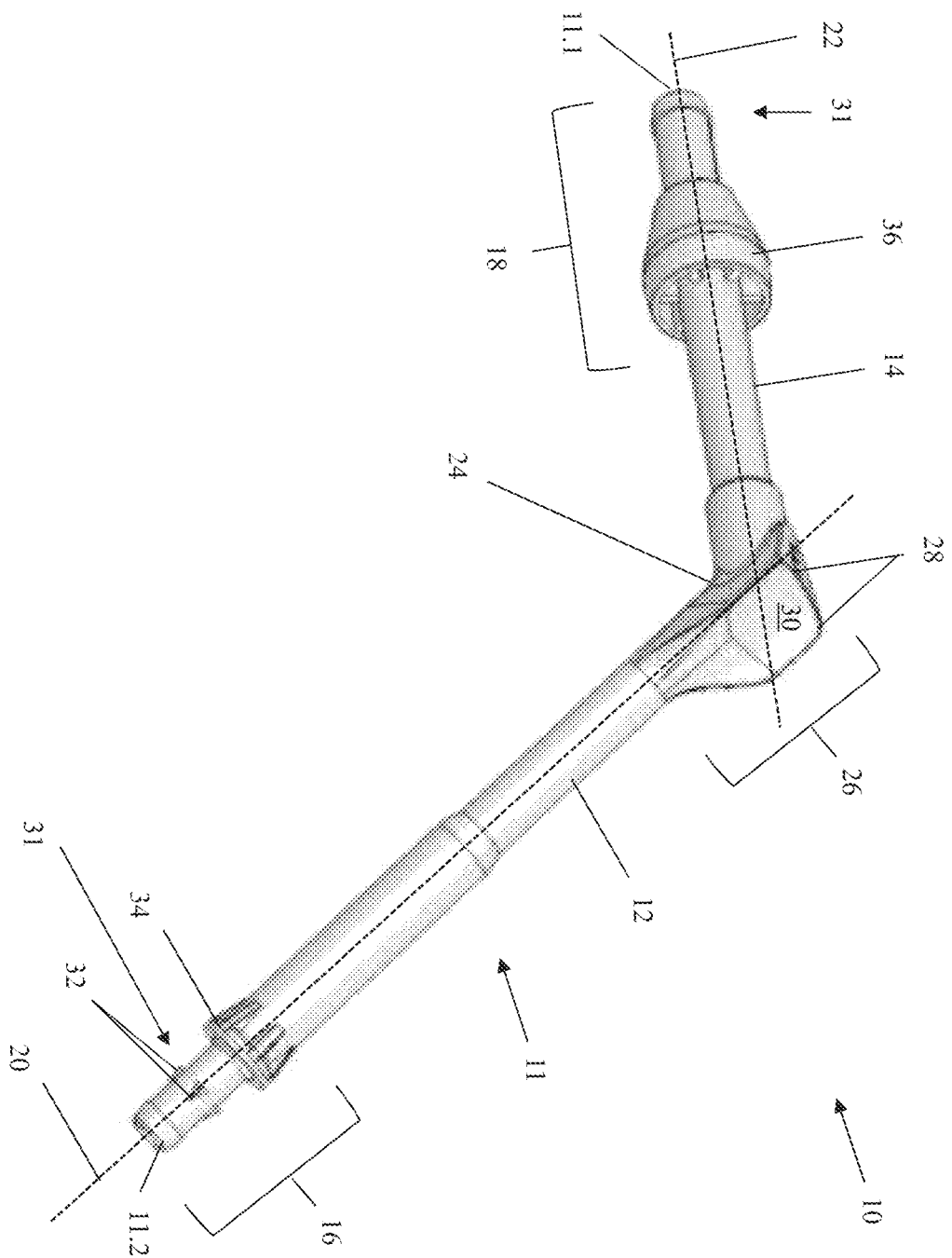
FIG. 3 shows a diagrammatic perspective view of a second embodiment of the device according to the invention.
Figure 4:
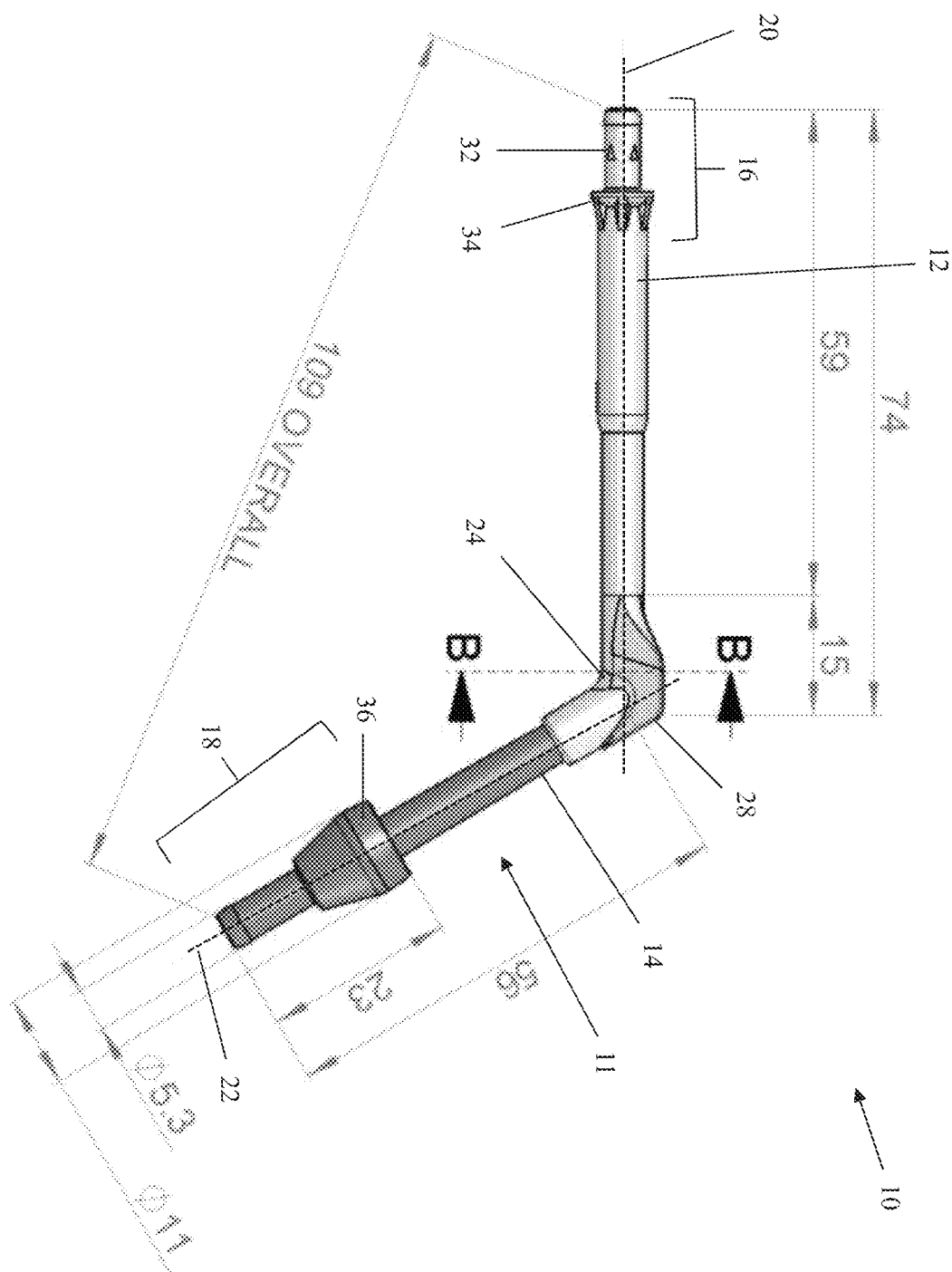
FIG. 4 shows a diagrammatic side view of a second embodiment of the device according to the invention.
Figure 5:
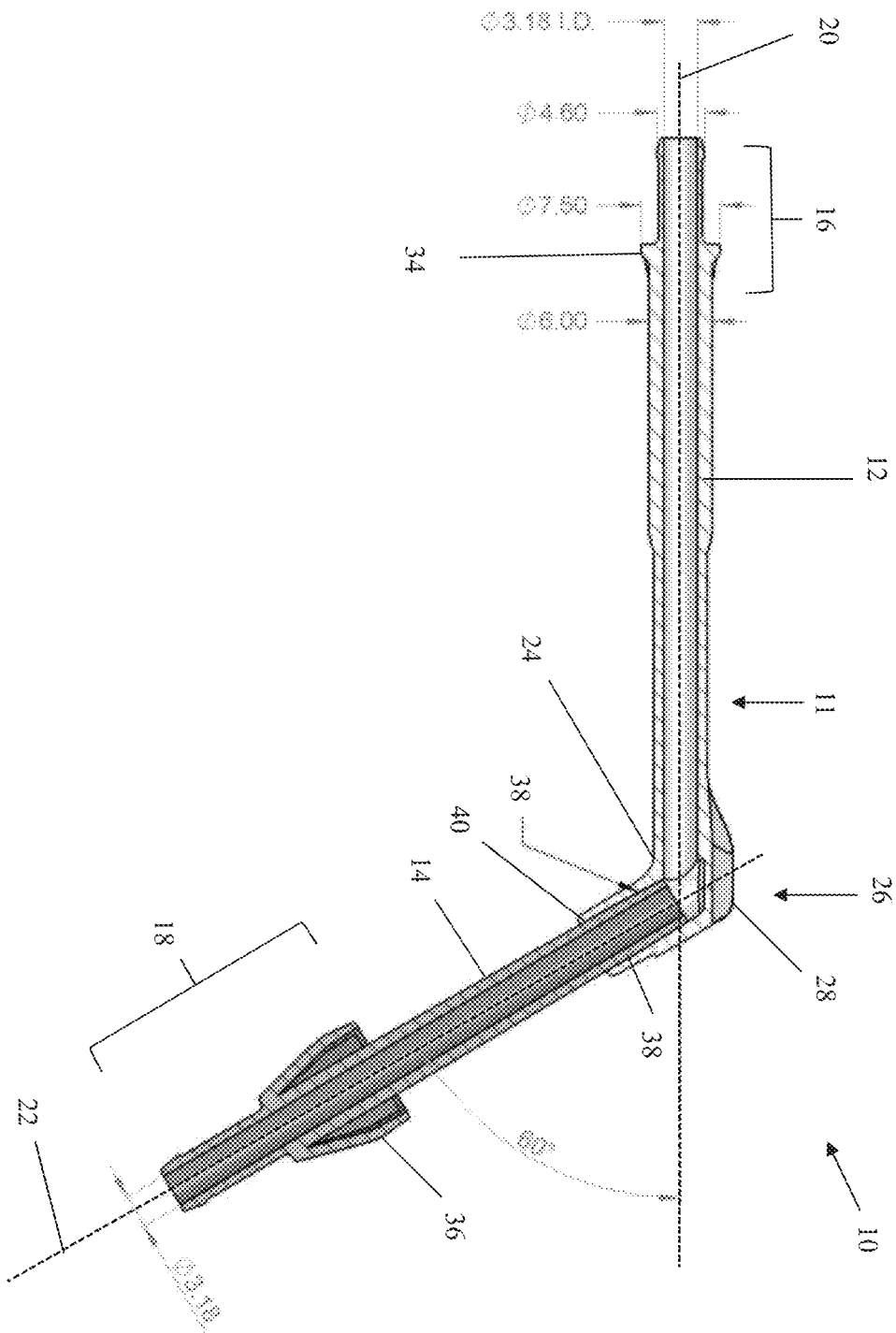
FIG. 5 shows a diagrammatic longitudinal section view of a second embodiment of the device according to the invention, showing the attached male end and female end of the separately manufactured internal and external legs.
Figure 6A:
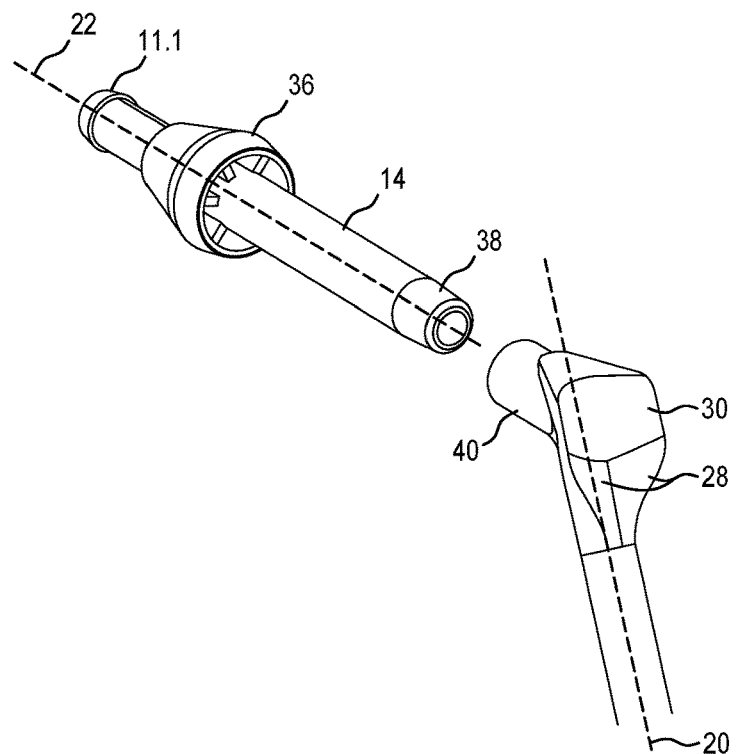
FIG. 6 shows (A) a diagrammatic perspective view of separately manufactured internal and external legs of a second embodiment of the device, showing the male and female ends and (B) a photograph of an assembled second embodiment of the device.
Figure 6B:
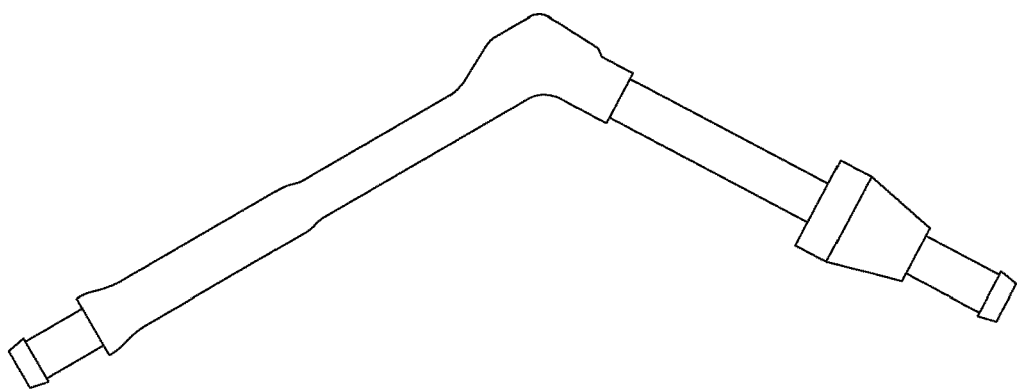
Figure 7A:
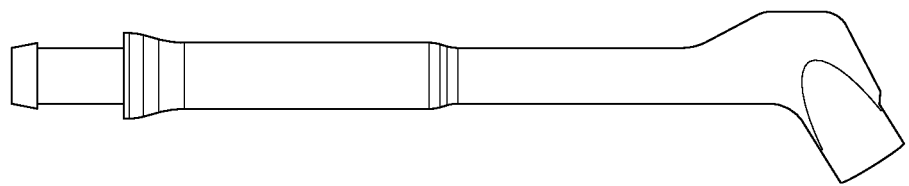
FIG. 7 shows (A) a photograph of the separately manufactured internal leg of the second embodiment of the device showing the distal end portion without hooks and (B) a close up photograph of the distal end portion shown in (A)
Figure 7B:
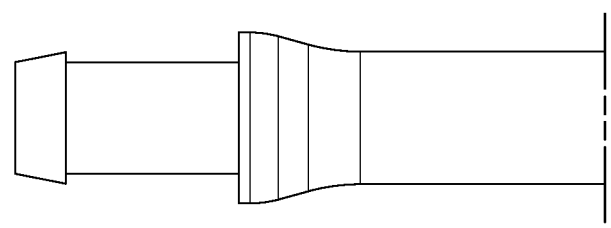
Figure 8A:
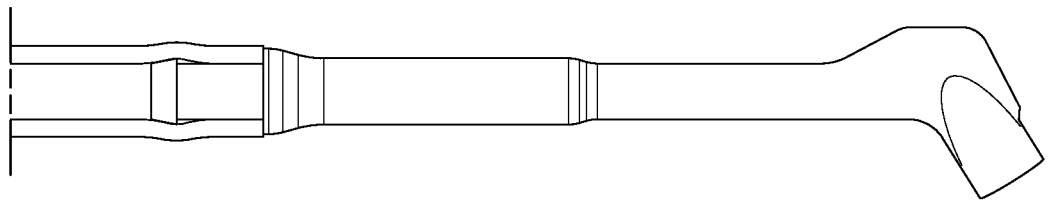
FIG. 8 shows (A) a photograph of the separately manufactured internal leg of the second embodiment of the device without hooks of FIG. 7A connected to internal tubing and (B) a close up photograph of the distal end portion shown in (A) showing the smooth continuous external surface formed.
Figure 8B:
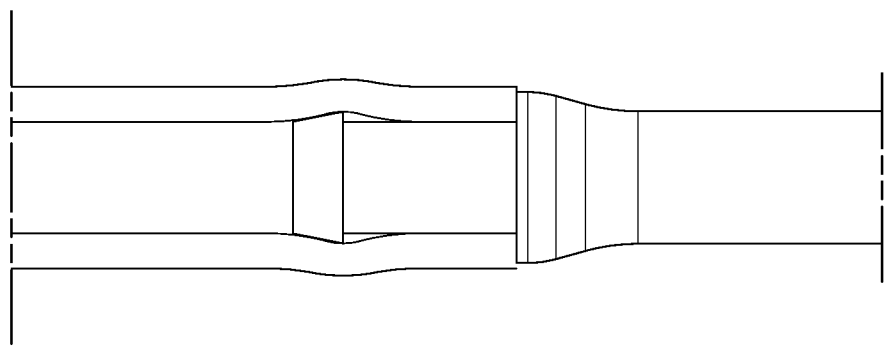
Figure 9A:
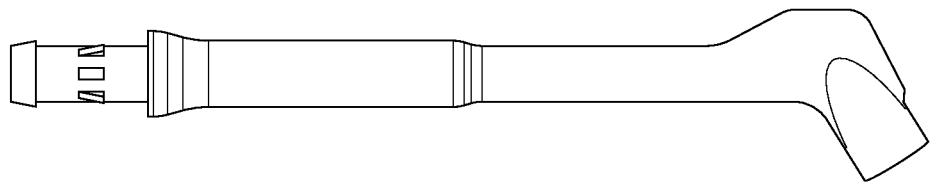
FIG. 9 shows (A) a photograph of the separately manufactured internal leg of the second embodiment of the device showing the distal end portion with hooks and (B) a close up photograph of the distal end portion shown in (A)
Figure 9B:
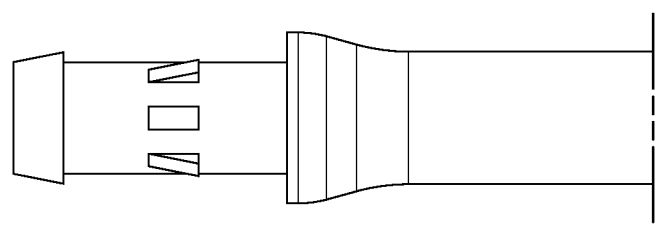
Figure 10A:
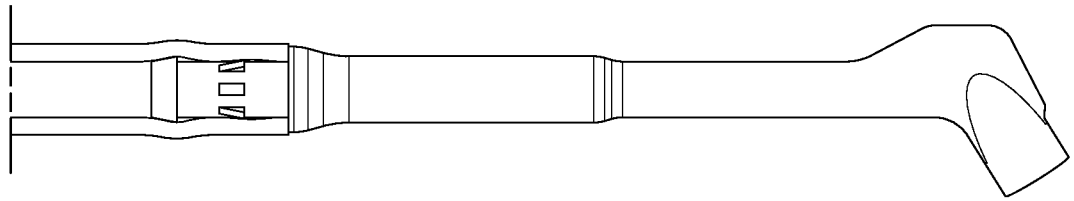
FIG. 10 shows (A) a photograph of the separately manufactured internal leg of the second embodiment of the device with hooks of FIG. 9A connected to internal tubing and (B) a close up photograph of the distal end portion shown in (A) showing the smooth continuous external surface formed.
Figure 10B:
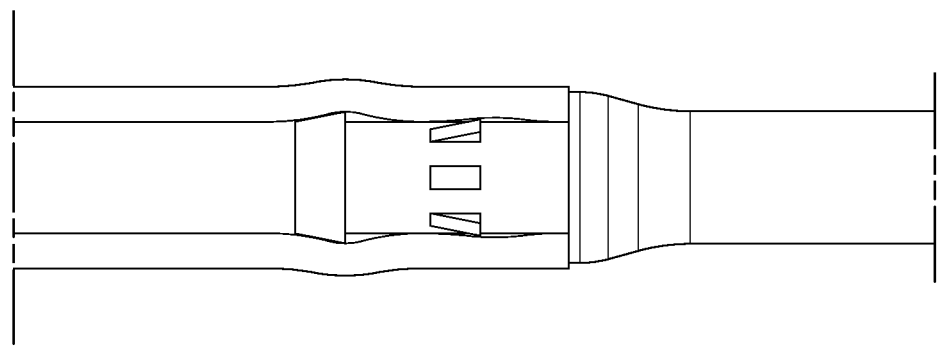

In the second embodiment shown in FIGS. 3 to 5, the device (10) is 109 mm in total length and comprises an elongate hollow internal leg (12) and an elongate hollow external leg (14). The internal leg (12) is about 74 mm in length and has a distal end portion (16) which is adapted to connect to internal tubing (19.2). The external leg (14) is about 58 mm in length and has a proximal end portion (18) which is adapted to connect to external tubing (19.3). The internal leg (12) has an internal leg axis (20) extending through the centre thereof, and the external leg (14) has an external leg axis (22) extending through the centre thereof.

Figure 1B:
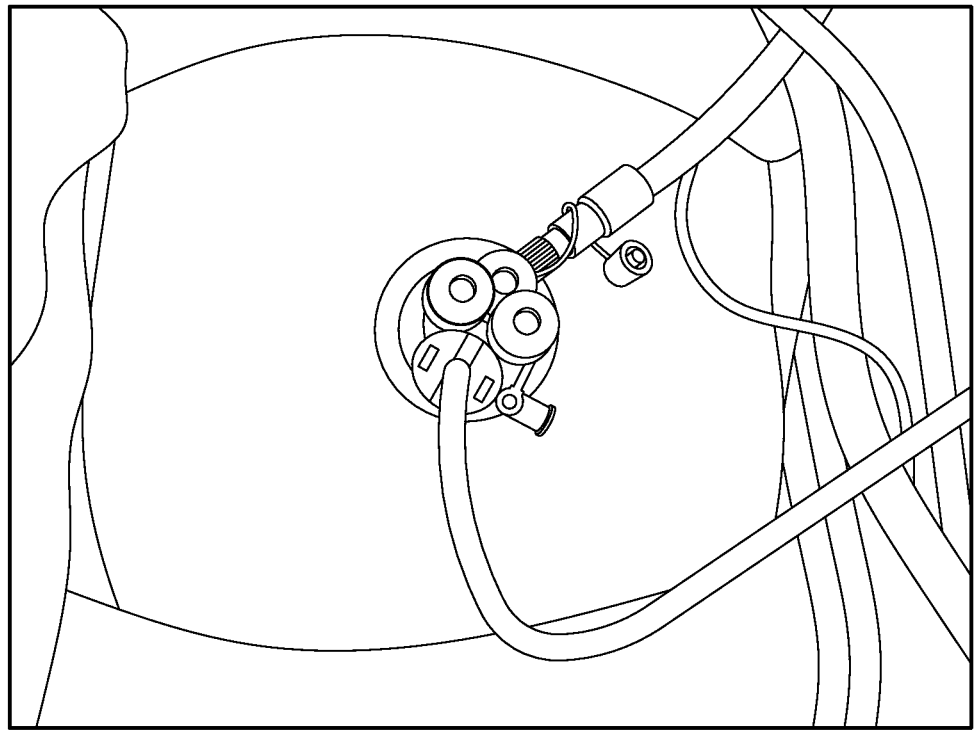
Figure 2:
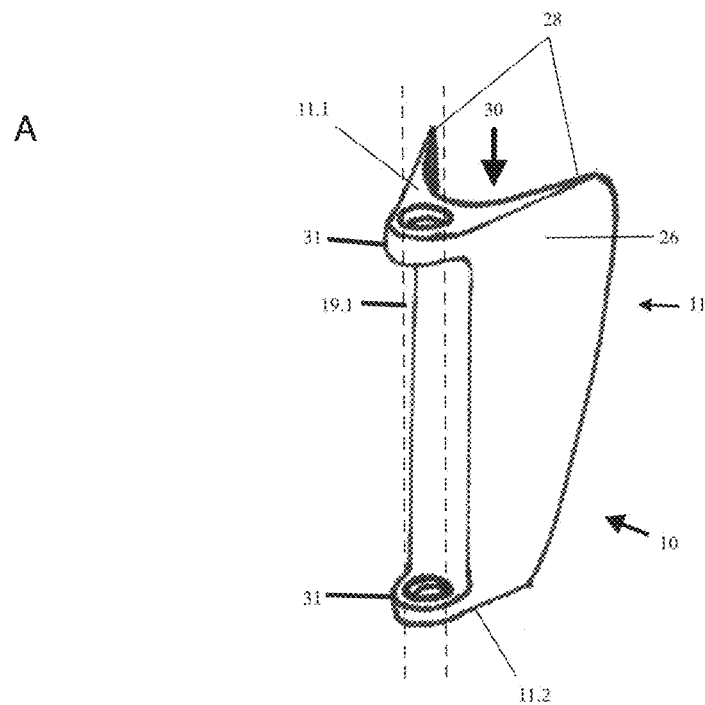
FIG. 2 shows a diagrammatic perspective view of a first embodiment of the device according to the invention.
Figure 2:
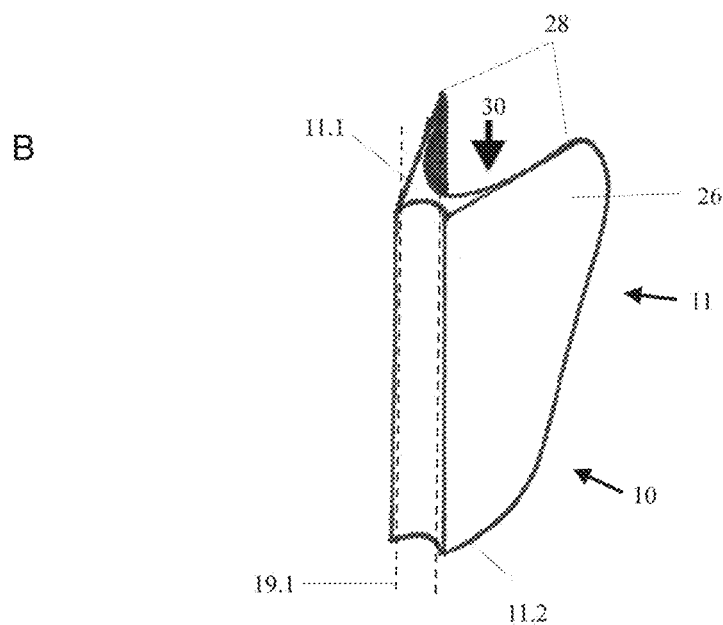
Figure 12A:
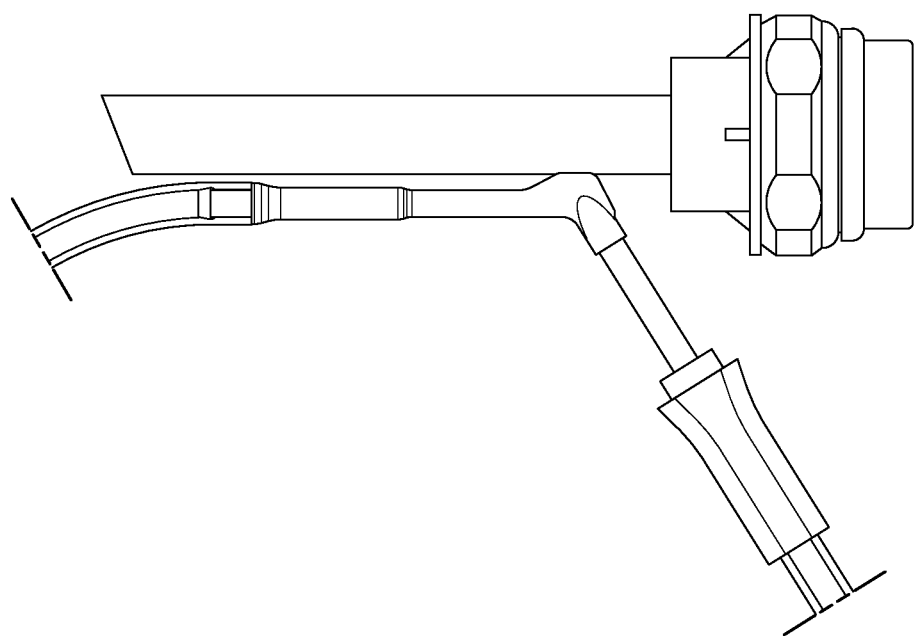
FIG. 12 shows (A) a side view photograph of the assembled second embodiment of the device, with the distal end portion connected to internal tubing and the proximal end portion connected to external tubing, placed adjacent to and abutting a laparoscopic trocar and (B) a perspective view photograph of the assembled second embodiment of the device and trocar shown in (A)
Figure 12B:
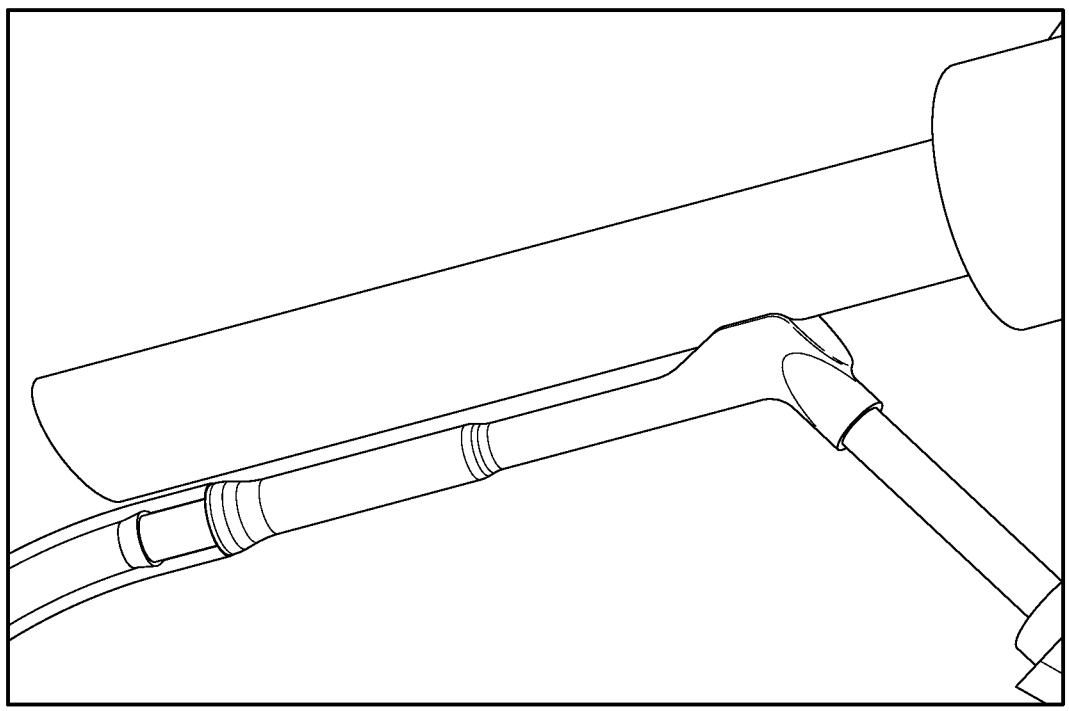

The second embodiment of the device (10) has a bend (24) which is located intermediate between the proximal end portion (18) in the distal end portion (16). In this embodiment, the bend (24) is an angular bend, such that the angle of intersection between the internal leg axis (20) and the external leg axis (22) is about 120 degrees, or 60 degrees from the vertical. It will be appreciated that the bend (24) in the device (10) results in the angulation of the external leg (14) from the internal leg (12), so that when the internal leg (12) is oriented in a vertical plane, the external leg (14) is stably angled away from the vertical plane, the proximal end portion (18) to which external tubing (19.3) is attached is accordingly positioned away from the vertical plane. As described further herein, this advantageously prevents the external leg (14) of the device (10) from clashing with or pressing against the external sealing portion of the laparoscopic trocar (17) (see FIGS. 12A and 12B) or against other trocars within a single incision multi-port device such as the SILS™ port (FIGS. 19A and 19B). The advantage of using this device in a SILS™ port is shown when comparing FIG. 1B with 19A and 19B.

The second embodiment of the device (10) has an abutment portion (26) that is located intermediate the bend (24) and the distal end portion (16). That is, the abutment portion (26) is positioned between the internal leg (12) and the bend (24).

The abutment portion (26) comprises a flange or collar, which defines a channel (30) shaped to receive the side of a trocar (17), such as a laparoscopic trocar. In this embodiment, the flange or collar is in the form of a pair of integral outwardly flaring wings (28) which between them define an elongate curved surface or channel (30). The wings (28) are about 20 mm in length and define a channel (30) that is about 20 mm in length and 11 mm in radial width.

The flange, collar, or pair of wings (28) in the second embodiment is rigid for simplicity of manufacture, but in other embodiments, such as the first embodiment is manufactured to be flexible, conformable and/or deformable. The pair of wings (28) may be formed from flexible material which adapts itself to conform to the side of the trocar (17) when the device (10) is braced against it. Alternatively, the flange, collar, or pair of wings (28) is inflatable, with a fluid including gas or liquid, or with gel material and, when filled with fluid or the gel material, forms a flexible abutment portion (26) that is capable of adapting the shape of its surface to correspond to the side of the trocar, when braced against it.

In some embodiments, such as the first embodiment, the abutment portion (26) may be integral with the elongate body (11). In other embodiments, such as the second embodiment, the abutment portion (26) may be detachable from the internal leg (12) of the elongate body (11) and attachable to the internal leg (12) intermediate the distal end portion (16) and the bend (24). The abutment portion (26), whether detachable or not, may be slidably displaceable along the internal leg (12), such that it may be moved along the length of the internal leg (12) and fixed into position at a desired location.

In the second embodiment, the distal end portion (16) comprises hooks (32) or barbs for engaging the internal tubing (19.2). The hooks (32) or barbs are radially disposed around the outer wall of the internal leg (12), and spaced from the end thereof. The distal end portion (16) also has an annular shoulder (34) or stop that is located intermediate the hooks (32) and the abutment portion (26). In some embodiments the annular shoulder (34) is in the form of an integral outwardly facing continuous collar which is spaced from the hooks (32). The annular shoulder (34) is shaped and dimensioned to correspond to the end of the internal tubing (19.2), so that in use, the tubing (19.2) is pushed onto the distal end portion (16) and braced against the annular shoulder (34) forming a smoothly continuous surface as shown in FIGS. 8A and 8B and FIGS. 10A and 10B. The external diameter of the annular shoulder (34) may be about 7.5 mm.

Figure 11A:
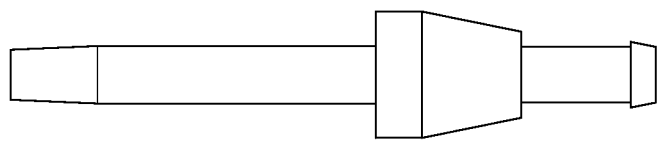
FIG. 11 shows (A) a photograph of the separately manufactured external leg of the second embodiment of the device showing the proximal end portion; (B) a photograph of the separately manufactured external leg shown in (A) connected to tubing of the same dimensions as the internal tubing; and (C) a close up photograph of the separately manufactured external leg shown in (A) connected to standard operation theatre suction tubing.
Figure 11B:
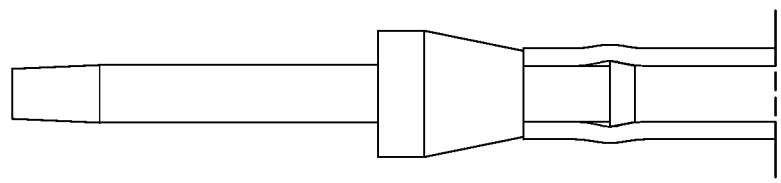
Figure 11C:
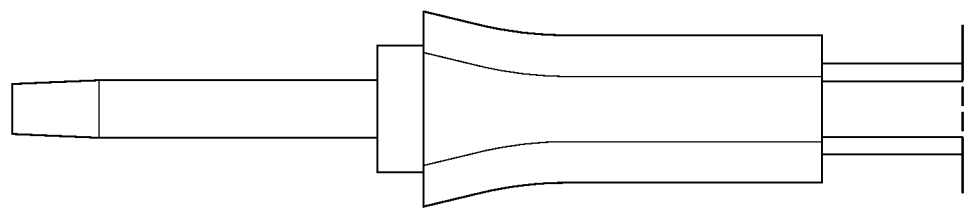

The proximal end portion (18) comprises a widened portion (36) for engaging the external tubing. The widened portion (36) is spaced from the end of the external tubing (19.3) and is shaped and dimensioned to correspond to the connection end of standard external operating theatre suction hose (FIG. 11C). Optionally, a section of internal tubing (19.2) may be cut and joined to the proximal end portion (18) at its narrower tip. In this case, the end of the narrower external tubing (19.3) is pushed onto the tip of the proximal end portion (18), and braces against the widened portion (36) (FIG. 11B), however the other end of that length of narrower tubing (19.3) must be connected to standard external operating theatre suction hose with a separate conventional connector.

The internal tubing (19.2) and external tubing (19.3) are typically silicone tubing, or other tubing that is usually used in surgical procedures. The internal tubing (19.2) used in this embodiment has an outer diameter of 6.35 mm and an inner diameter of 3.18 mm. A standard external operating theatre suction tubing (female) connector has an inner diameter of about 9 mm, but is designed to stretch over and seal against a standard slightly wider male connector. The 10.5 mm diameter of the widened portion (36) therefore accommodates standard 9 mm tubing.

Figure 13:
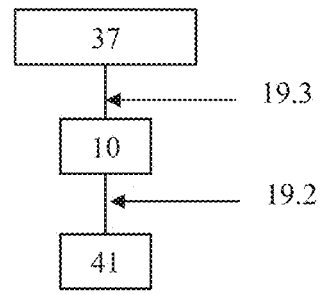
FIG. 13 shows (A) shows a diagrammatic representation of a kit of the second embodiment of the device of the invention with a suction source and a retractor and (B) a diagrammatic representation of a kit of the second embodiment of the device of the invention with a suction source, a saline irrigator, and optionally a $CO_2$ blower and an internal sucker-irrigator device.
Figure 13:
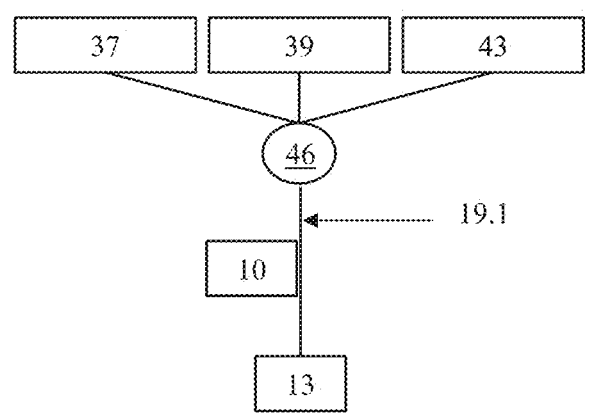

As shown in FIG. 13A, the kit of the invention comprises a suction source (37) with a canister which is connected to external tubing (19.3) which in turn is connected to the second embodiment of the device (10). The device (10) is connected to internal tubing (19.2) which is connected to a retractor (41). FIG. 13B shows a kit of the invention comprising a first embodiment of the device (10) which is attached to tubing (19) that is connected to a suction nozzle tip (13) and a suction source (37) including a canister, to a saline irrigator (39), and/or optionally to a $CO_2$ source (43). A selector or controller (46) may be used to select whether the suction source (37), the saline irrigator (39), and/or the $CO_2$ source (43) is to be used.

Figure 22A:
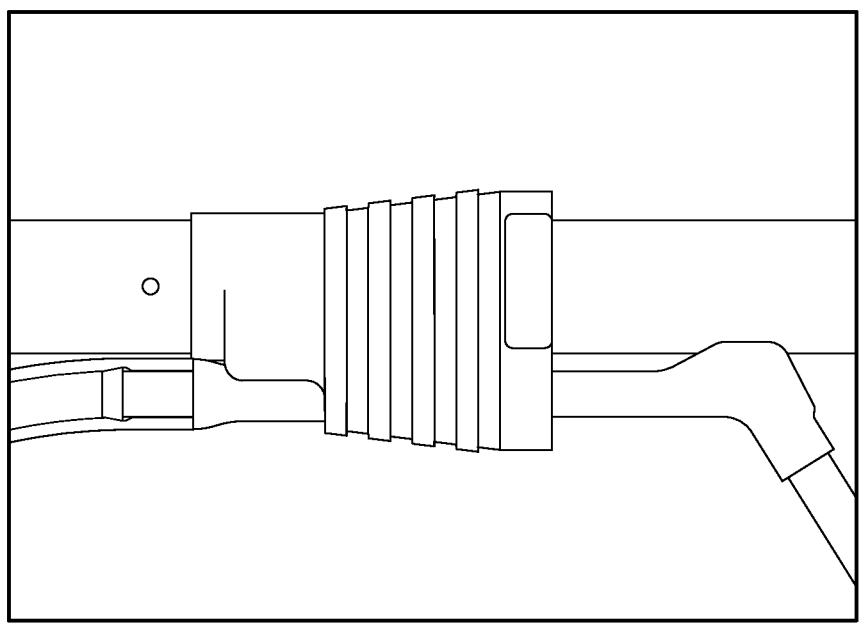
FIG. 22 shows (A) a side view photograph of a 12 mm trocar and the second embodiment of the device of the invention in the LiVac™ Bevel; and (B) a diagrammatic perspective view of (A).
Figure 22B:
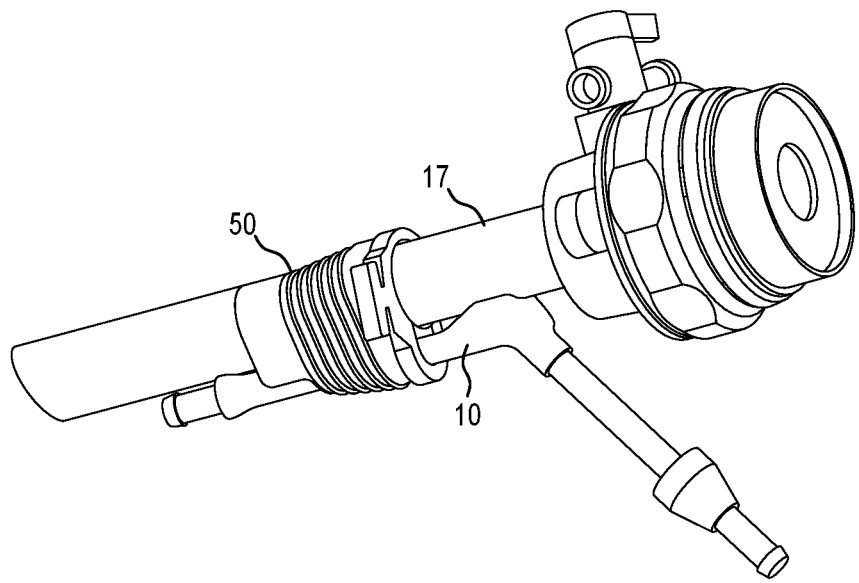

The second embodiment of the device (10) may further comprise a plug portion (not shown) which is located on the internal leg (12), here represented with a 6 mm outer diameter. The plug portion is in the form of an integral wider portion which, when placed within suitable tubular housing, substantially fills the lumen, and braces against the internal walls of the housing to substantially seal it. Such housing includes the commercially available LiVac™ Bevel (50) as shown in FIGS. 22A and 22B.

The device (10) in the second embodiment is made from polycarbonate material, such as Lexan or other suitable material as selected by one skilled in the art. These may include polylactic acid (PLA), acrylonitrile butadiene styrene (ABS), nylon or high-density polyethylene (HDPE) and is usually about 109 mm in length, with a maximum external diameter of about 10.5 mm. The widened portion (36) is within 23 mm of the end of the external leg (14), and has an external diameter of 10.5 mm, while the external diameter of the main section of the external leg (14) is about 5.3 mm.

Some embodiments of the device (10) may be manufactured as a single integral body, such as using injection molding processes according to standard procedures. Other embodiments are manufactured by 3-D printing according to standard procedures.

The second embodiment of the device (10) shown here is manufactured in part, as shown in FIGS. 6 to 12, according to a method comprising the steps of producing the internal leg (12) with the distal end portion (16) and a first corresponding end, in this embodiment a female end (40), producing the external leg (14) with the proximal end portion (18) and a second corresponding end, in this embodiment a male end (38) and inserting the male end (38) into the female end (40). The male end (38) and the female end (40) are correspondingly tapered by 2 degrees to facilitate the insertion, and adhesive is applied to the inside of the female end (40) and to the outside of the male end (38).

The abutment portion (26) may be made from a range of bio-compatible materials having flexible, malleable, and/or conformable properties, as selected by one skilled in the art. In those embodiments, it is necessary to manufacture the abutment portion (26) separately from the other components of the device (10), such as the internal leg (12) and the external leg (14), and assemble the components after manufacture. Furthermore, areas of the device (10) which are expected to withstand tensile stress, such as the bend (24), may be reinforced with additional material during manufacture.

The device (10) is capable of being sterilised. In some embodiments, it is a disposable device (10), capable of being sterilised and packaged individually for one-time use. In other embodiments, it is machined from surgical grade steel, and is sterilisable and re-usable.

In some embodiments the device (10) is supplied on its own. In other embodiments, the device (10) is supplied as a kit which comprises the device (10) and tubing (19.1, 19.2, 19.3), and/or a suction or fluid source, and/or a surgical apparatus such as a sucker-irrigator (13) and/or a retractor (41), as shown in FIGS. 13A and 13B.

Figure 14:
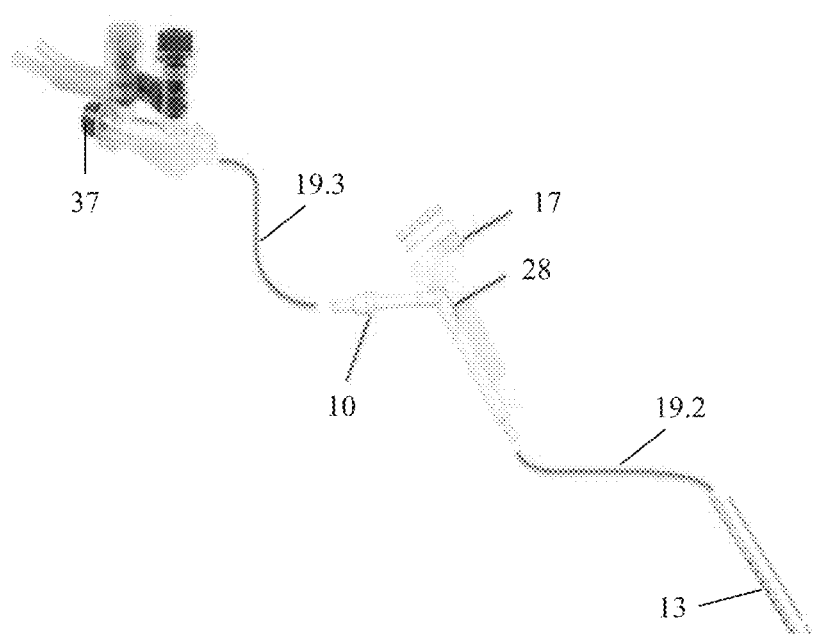
FIG. 14 shows (A) the set up of a kit of the invention including a second embodiment of the device of the invention as shown in FIG. 13A, and (B) the set up of a kit of the invention including a first embodiment of the device of the invention as shown in FIG. 13B.
Figure 14:
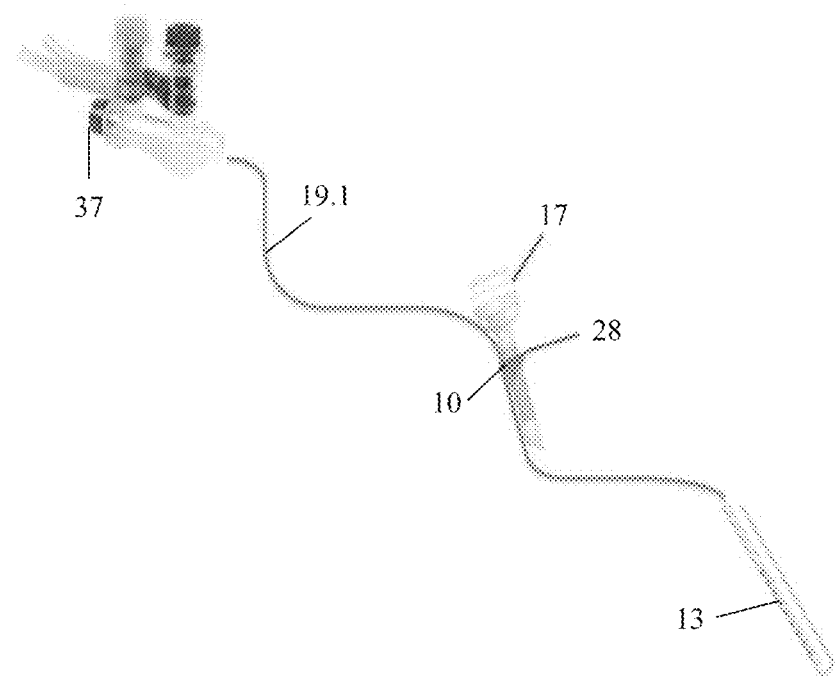

In use, the device (10) is employed in laparoscopic surgical procedures. Typically, the first embodiment is used with suction-irrigation apparatus (13, 19.1, 37, 39) and the second embodiment, which can withstand greater compressive forces, is used with retraction suction apparatus (19.2, 19.3, 37, 41). However, both the first and the second embodiments may be used with suction-irrigation apparatus. In some applications, the device (10) is connected to internal silicone tubing (19.2) which in turn is connected to a rigid internal nozzle tip (13). Where the device (10) is in the form of the first embodiment, such as in FIG. 14A, the device (10) is laterally attached to the tubing (19.1) either by glue or clasps (not shown). Where the device (10) is in the form of the second embodiment, such as in FIG. 14B, the internal leg (12) is attached to the internal tubing (19.2) and the external leg (14) is attached to the external tubing (19.3). The device (10) abuts a laparoscopic trocar such that the wings (28) fit against and around the side of the trocar (17), thereby minimising the opposing gaps formed on either side of the device (10) and between the device (10) and the trocar (17), when the device (10) and the trocar (17) are placed longitudinally adjacent to one another.

In use, the first embodiment of the device (10) is inserted into an incision in the abdomen of the patient according to a method (not shown) comprising the steps of inserting a trocar (17) into the incision, withdrawing the trocar (17) from the incision, inserting tubing (19.1) into the incision the tubing optionally comprising a sucker-irrigator apparatus or nozzle tip (13), inserting the device (10) into the incision, and inserting a trocar (17) adjacent to the device (10) until the side of the trocar (17) is received by the abutment portion (26). The first embodiment of the device (10) may be attached to the tubing (19.1) either before or after insertion into the incision.

In embodiments comprising at least two pairs of wings (28) which are different in dimension, with a smaller pair of wings (28.2) disposed towards the proximal end (11.1) and a larger pair of wings (28.1) disposed towards the distal end (11.2), the smaller pair of wings (28.2) defines a relatively shallower channel (30.2) than the relatively deeper channel (30.1) defined by the larger pair of wings (28.1). The relatively shallower channel (30.2) is adapted to receive a longitudinally adjacent trocar (17) of relatively smaller diameter, such as a 5 mm trocar. The deeper channel (30.2) is adapted to receive a longitudinally adjacent trocar (17) of larger diameter, such as a 12 mm trocar. In use, this embodiment is inserted into a incision in the abdomen of the patient as described above, except that when inserting the trocar (17) adjacent to the device (10) until the side of the trocar (17) is received by the abutment portion (26), the device (10) is moved relative to the trocar (17) such that the smaller pair of wings (28.2) engages the trocar (17) when the trocar is relatively smaller in diameter, such as a 5 mm trocar. Similarly, the larger pair of wings (28.1) engages the trocar (17) when the trocar (17) is relatively larger in diameter, such as a 12 mm trocar. It will be appreciated that when the trocar of larger diameter is used, the device (10) is inserted further into the incision in the patient to permit abutment of the larger pair of wings (28.1) with the trocar (17).

Figure 15:
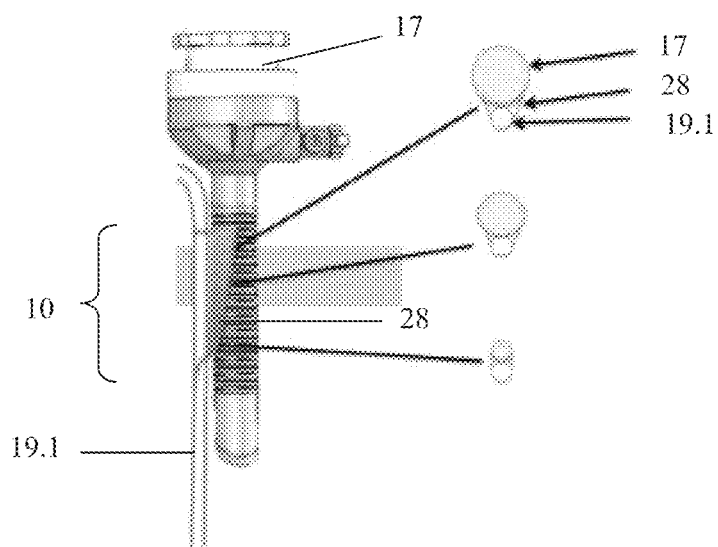
FIG. 15 shows a diagrammatic representation of the first embodiment of the device of the invention in use with (A) a trocar of larger diameter and (B) a trocar of smaller diameter, with insets showing cross-sections of the abutment between the device and the trocar.
Figure 15:
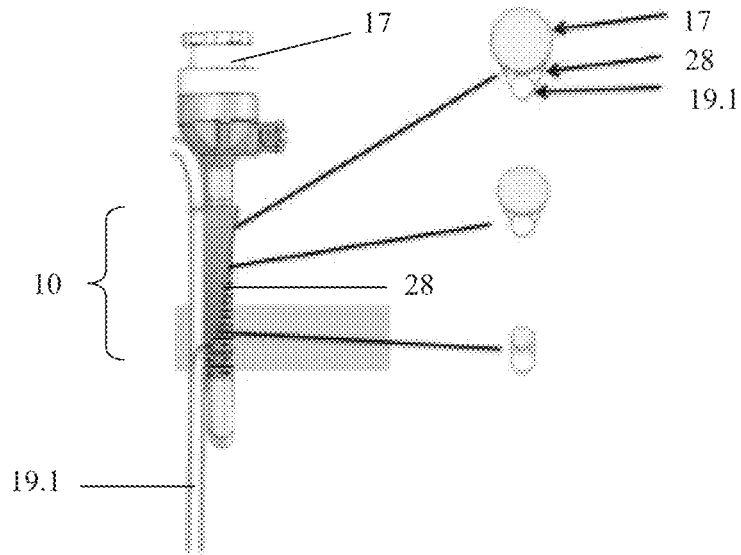

In embodiments where the dimensions of the wings (28) of the abutment portion (26) are longer at the proximal end (11.1) than at the distal end (11.2) of the elongate body (11), a relatively deeper channel (30) defined at the proximal end (11.1) of the elongate body (11) is adapted to receive a longitudinally adjacent trocar (17), of larger diameter. This is shown in FIG. 15A. Similarly, a relatively shallower channel (30) defined by the wings (28) at the distal end (11.2) of the elongate body (11) is adapted to receive a longitudinally adjacent trocar (17) of smaller diameter, as shown in FIG. 15B.

Figure 18A:
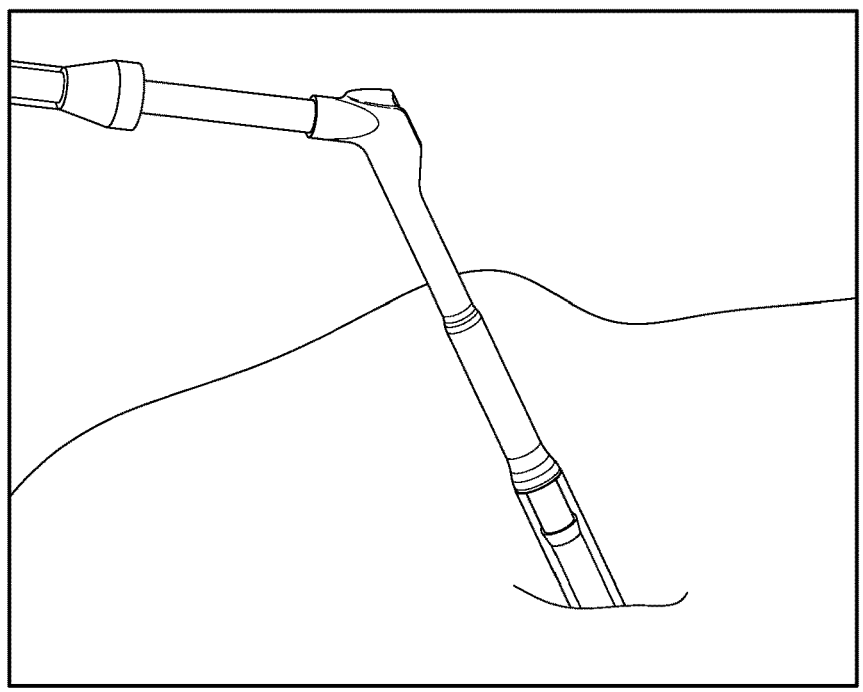
FIG. 18 shows (A) a photograph of the second embodiment of the device in which the distal end portion of the internal leg is inserted into internal tubing passing through an incision in a piece of pork belly and (B) a photograph of the device inserted into the incision until the bend reaches or abuts the incision the distal end portion, adjacent to a 12 mm Covidien trocar which has been inserted into the incision until the side of the trocar is received by the abutment portion.
Figure 18B:
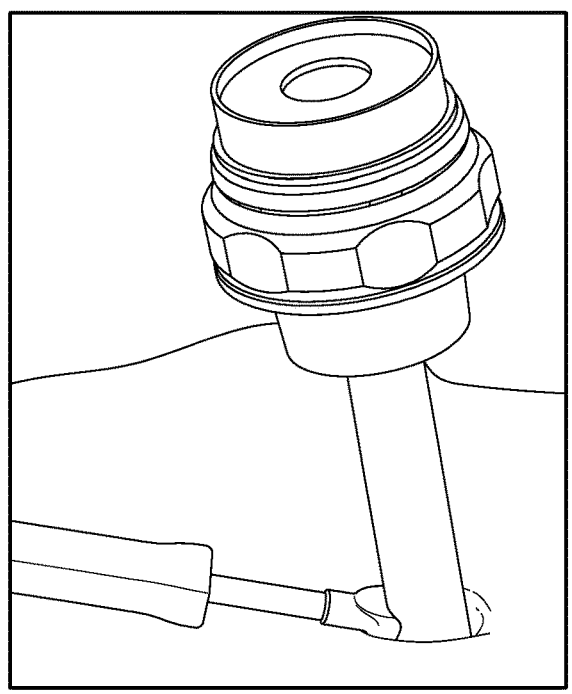
Figure 19:
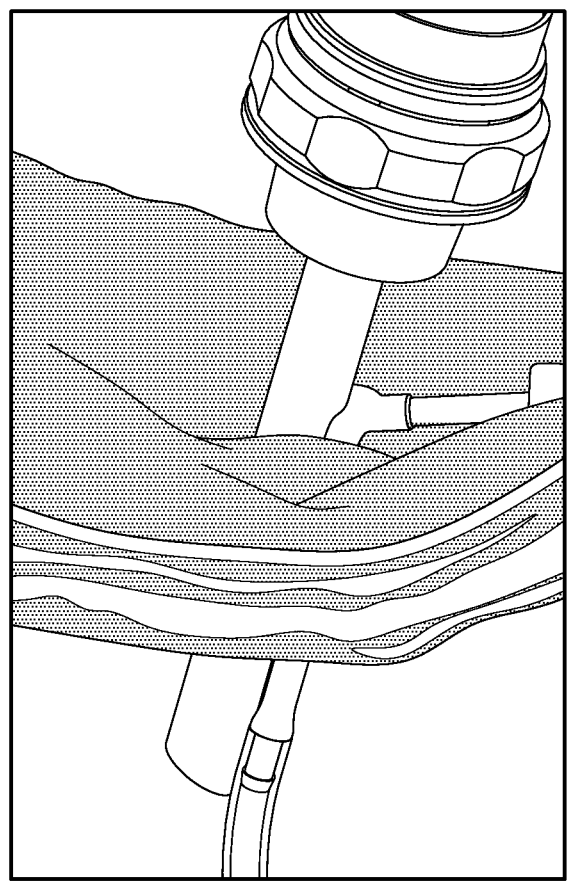
FIG. 19 shows a photograph of the side of the piece of pork belly with the second embodiment of the device shown in FIG. 18B.
Figure 20A:
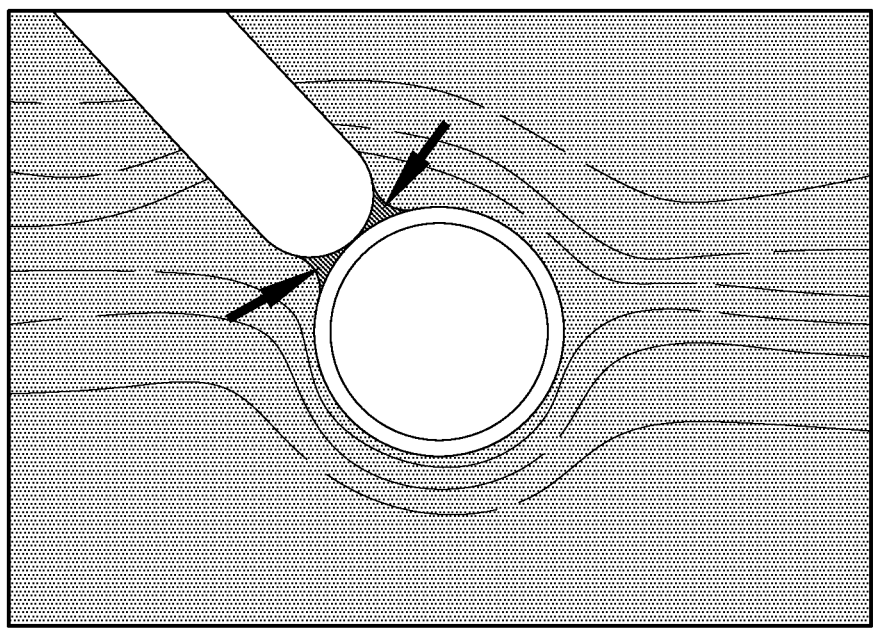
FIG. 20 shows (A) a close up photograph of the underside of the piece of pork belly with the second embodiment of the device shown in FIG. 18B demonstrating the gap between the second embodiment of the device and adjacent trocar (arrows) through which $CO_2$ could potentially escape, and (B) a close up photograph of the external incision in the pork belly with the second embodiment of the device shown in FIG. 18B, demonstrating how the wings substantially fill the gaps formed on either side of the second embodiment of the device and between the second embodiment of the device and the margins of the incision, thereby limiting any leakage of $CO_2$.
Figure 20B:
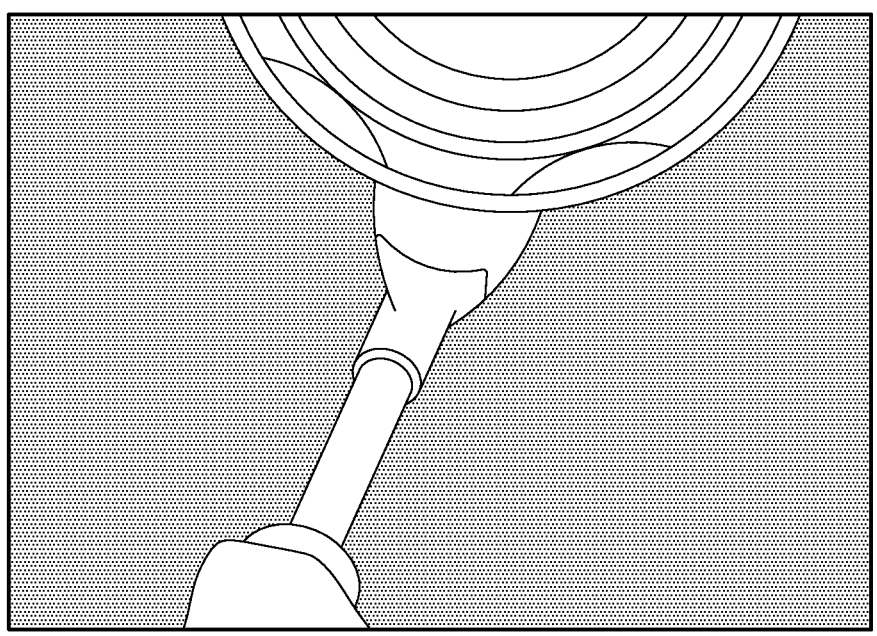
Figure 21A:
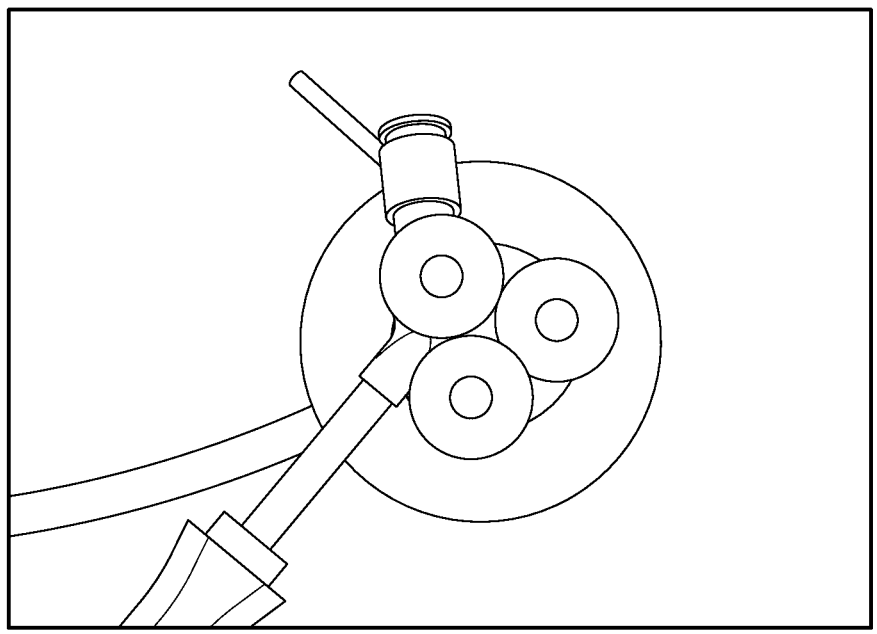
FIG. 21 shows (A) a top view photograph of the arrangement of laparoscopic apparatus in a SILS™ port, together with a second embodiment of the device of the invention; and (B) a perspective view photograph of the arrangement of (A)
Figure 21B:
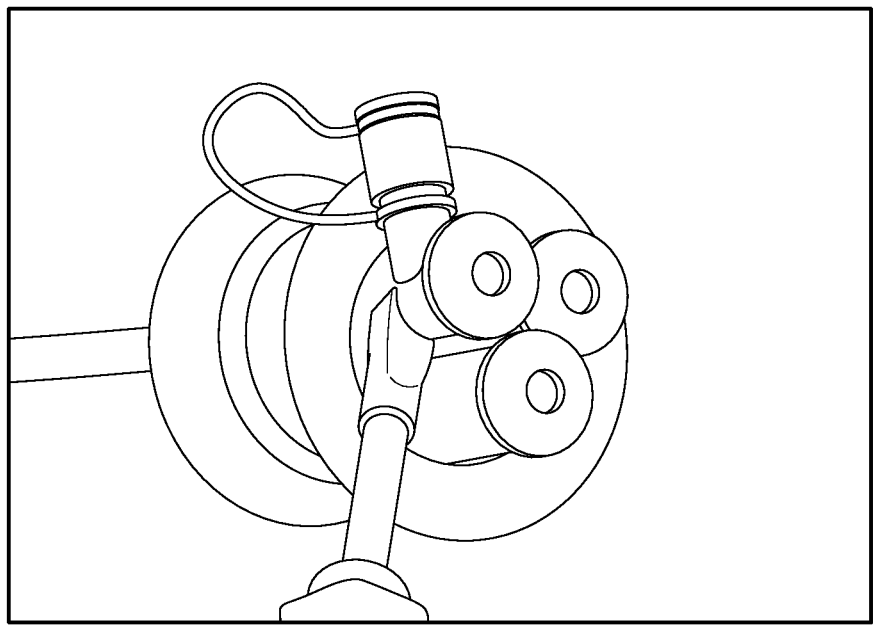

As illustrated in FIGS. 18 to 20, using a piece of pork belly to simulate the abdominal wall of a patient, the distal end portion (16) of the internal leg (12) is inserted into internal tubing (19.2) (FIG. 18A), then the internal leg (12) with the internal tubing (19.2) is inserted into an incision in the abdomen of a patient, until the bend (24) and the wings (28) reaches or abuts the incision. The internal tubing (19.2) is connected to an internally located apparatus, such as a retractor (41). A port (17), such as a 12 mm Covidien trocar is then inserted into the incision adjacent to the device (10), until the side of the port (17) presses against the device (10), or is received by the abutment portion (26) (FIG. 18B and FIGS. 19 and 20B). The proximal end portion (18) is then inserted into external tubing (19.3), which is connected to a suction (37) or fluid (39) source. The suction (37) or fluid (39) source is activated by the user, to deliver suction to the internally located apparatus, the retractor (41).

In another embodiment, the internally located apparatus is a sucker-irrigator (13) which is connected to tubing (19.1) which may be connected to a controller (46) linked to a suction source (37), a saline irrigator (39) and optionally a $CO_2$ source (43). A user activates the controller (46) to determine whether suction is applied for the evacuation of fluids and/or vapours, or irrigation (typically saline) to lavage the surgical field (FIG. 13B). A user selects suction or irrigation through a trumpet-valve actuator or controller handpiece or footpiece.

In another embodiment, the internally located apparatus blows $CO_2$ through the controller (46). This assists with clearing fluids from the user's field of view.

It will be appreciated that the device (10) has a smaller diameter than the trocar (17), and when the device (10) is braced against the trocar (17) within an incision in a patient, the wings (28) will tend to conform against and around the side of the trocar (17), thereby substantially filling the gaps formed on either side of the device (10) and between the device (10) and the margins of the incision (FIGS. 15A and B).

Among the significant advantages of the second embodiment of the device (10) of the present invention is the minimising, reduction, or elimination of compression and collapsing under suction where the device (10) passes through the incision, either adjacent to a trocar or within the LiVac™ Bevel or single incision port such as a SILS™ port, in place of the conventionally used compressible internal tubing. This facilitates in minimising, reducing, or eliminating interruptions in the suction provided to the retractor, and increases the efficiency of tissue retraction.

The use of the device (10) of the invention also minimises and reduces leakage of insufflation gas from the body cavity of a patient during surgery, as the wings (28) substantially fill the gaps formed on either side of the device (10) and between the device (10) and the margins of the incision. This has benefits in reducing the amount of insufflation gas required to be pumped into the body cavity of the patient during surgery, and the expense and risks associated therewith, as well as reducing interruptions and inconvenience to the surgeon in the reduction of the pneumoperitoneum caused by leakage of insufflation gas during surgery.

Furthermore, the angulation of the second embodiment of the device (10) such that the proximal end is oriented away from the vertical plane advantageously prevents the external leg (14) of the device (10) from clashing with or pressing against the external sealing portion of the laparoscopic trocar (see FIGS. 12A and 11B) or against other trocar within a single incision multi-port device such as the SILS™ port (FIGS. 18 and 19).

In embodiments where the device may be used with internally located apparatus is a sucker-irrigator (13), such as with the first embodiment, the device of the invention advantageously allows the sucker-irrigator (13) to remain internally located within the peritoneal cavity. An internally located sucker-irrigator (13), which does not have to be inserted and removed as often, reduces or eliminates the need to displace other instruments, and can be more rapidly deployed. It also does not require the insertion of an additional trocar, with the associated advantage of not requiring a further incision to be made in the patient. The first embodiment of the present invention also has the advantage of permitting the use of flexible tubing, which generally assists manipulation of instruments in laparoscopic surgery, as well as an optional rigid suction-irrigation nozzle which can be placed aside, within easy reach inside the peritoneal cavity, when not in use.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

The invention claimed is:

1. A surgical device comprising:
an elongate body with a proximal end and a distal end, the elongate body comprising an abutment portion comprising a pair of integral outwardly flaring elongate wings which between them define a channel adapted for receiving a longitudinally adjacent trocar, wherein the dimensions of the wings are longer at the proximal end than at the distal end of the elongate body, thereby defining a relatively deeper channel at the proximal end of the elongate body and a relatively shallower channel at the distal end of the elongate body; and
attachment means capable of attaching the elongate body to tubing.

2. The device according to claim 1, wherein the elongate body and the abutment portion are integral; optionally wherein the elongate body further comprises:
an elongate hollow internal leg comprising a distal end portion and an internal leg axis;
an elongate hollow external leg comprising a proximal end portion and an external leg axis; and
a bend intermediate the proximal end portion and the distal end portion wherein the internal leg and the external leg axes intersect.

3. The device according to claim 1, wherein the channel is shaped to receive a side of a longitudinally adjacent trocar.

4. The device according to claim 1, wherein the attachment means is selected from at least one of a clip or glue; optionally wherein the attachment means is capable of connecting the elongate body to tubing and comprises:
a distal end portion of an elongate hollow internal leg wherein the distal end portion is adapted to connect to internal tubing; and
a proximal end portion of an elongate hollow external leg wherein the proximal end portion is adapted to connect to external tubing.

5. The device according to claim 4, wherein the distal end portion comprises an annular shoulder for bracing against the internal tubing; optionally wherein the proximal end portion comprises a widened portion for engaging the external tubing.

6. The device according to claim 2, wherein the internal leg comprises a plug portion for bracing the device against the internal walls of co-axially extending tubular housing; optionally wherein the tubular housing is a laparoscopic single incision port or collar device; optionally wherein the angle of intersection of the internal leg and the external leg axes is between 90 degrees and 160 degrees, optionally 120 degrees.

7. The device according to claim 1, wherein the device is manufactured from an injection-moulded thermoplastic material, optionally wherein the pair of integral outwardly flaring elongate wings are manufactured from a bio-compatible material.

8. A method for inserting the device of claim 1 into an incision in a patient, the method comprising the steps of:
inserting a trocar into the incision;
withdrawing the trocar from the incision;
inserting the tubing into the incision, the tubing optionally connected to a sucker-irrigator apparatus;
inserting the device of claim 1 into the incision, optionally attached to the tubing; and
inserting the trocar into the incision adjacent to the device until the side of the trocar is received by the abutment portion.

9. A method for delivering suction or fluid to an internally located apparatus, the method comprising the steps of:
inserting a trocar into the incision;
withdrawing the trocar from the incision;
inserting the tubing into the incision, the tubing connected to the internally located apparatus;
inserting the device of claim 1 into the incision; and
inserting a trocar into the incision adjacent to the device until the side of the trocar is received by the abutment portion.

10. The method according to claim 9, wherein the internally located apparatus is a retractor or a sucker-irrigator.

* * * * *